United States Patent
Pawliszyn et al.

(10) Patent No.: US 9,870,907 B2
(45) Date of Patent: Jan. 16, 2018

(54) PROBE FOR EXTRACTION OF MOLECULES OF INTEREST FROM A SAMPLE

(71) Applicant: JP SCIENTIFIC LIMITED, Waterloo (CA)

(72) Inventors: Janusz B. Pawliszyn, Waterloo (CA); German Augusto Gomez Rios, Waterloo (CA)

(73) Assignee: JP Scientific Limited, Waterloo (CA)

( * ) Notice: Subject to any disclaimer, the term of this patent is extended or adjusted under 35 U.S.C. 154(b) by 77 days.

(21) Appl. No.: 14/738,678

(22) Filed: Jun. 12, 2015

(65) Prior Publication Data

US 2015/0318158 A1 Nov. 5, 2015

Related U.S. Application Data

(60) Continuation-in-part of application No. 14/705,238, filed on May 6, 2015, now abandoned, which is a
(Continued)

(51) Int. Cl.
*H01J 49/10* (2006.01)
*H01J 49/26* (2006.01)
(Continued)

(52) U.S. Cl.
CPC .............. *H01J 49/10* (2013.01); *B01J 20/286* (2013.01); *B01J 20/287* (2013.01); *G01N 1/405* (2013.01);
(Continued)

(58) Field of Classification Search
CPC .............. G01N 1/405; G01N 2030/009; G01N 2030/062; G01N 33/50; G01N 1/02;
(Continued)

(56) References Cited

U.S. PATENT DOCUMENTS

| 4,140,653 A | 2/1979 | Imura et al. |
| 4,476,231 A | 10/1984 | Deindoerfer |

(Continued)

FOREIGN PATENT DOCUMENTS

| CN | 2630850 Y | 8/2004 |
| CN | 102698720 | 10/2012 |

(Continued)

OTHER PUBLICATIONS

Mirnaghi, Fatemeh S., and Janusz Pawliszyn. "Reusable solid-phase microextraction coating for direct immersion whole-blood analysis and extracted blood spot sampling coupled with liquid chromatography—tandem mass spectrometry and direct analysis in real time—tandem mass spectrometry." Analytical chemistry 84, No. 19 (2012): 8301-8309.*

(Continued)

*Primary Examiner* — Wyatt Stoffa
(74) *Attorney, Agent, or Firm* — Borden Ladner Gervais LLP; David Nauman

(57) ABSTRACT

The present disclosure describes a device for generating ionized molecules for analysis in a mass spectrometer. The device includes: a mesh substrate coated with an extraction phase, the extraction phase comprising a polymer that absorbs a molecule of interest from a matrix, or a polymer and solid phase microextraction (SPME) particles having pores dimensioned to absorb a molecule of interest from a matrix, where the mesh substrate has a sufficiently open structure to allow fluid to flow through the mesh substrate; and a solid substrate connected to the mesh substrate to provide stability to the coated mesh substrate. Mass spectrometry systems that include such a device are also described. Methods of analyzing an analyte previously extracted from a matrix onto the device are also described.

21 Claims, 19 Drawing Sheets

Related U.S. Application Data continuation of application No. 13/478,295, filed on May 23, 2012, now abandoned, which is a division of application No. 12/174,494, filed on Jul. 16, 2008, now abandoned, which is a continuation-in-part of application No. 11/706,167, filed on Feb. 15, 2007, now Pat. No. 8,008,064, which is a continuation of application No. 11/208,933, filed on Aug. 23, 2005, now Pat. No. 7,232,689, which is a continuation-in-part of application No. 10/506,827, filed as application No. PCT/CA03/00311 on Mar. 6, 2003, now Pat. No. 7,384,794.

(60) Provisional application No. 61/997,937, filed on Jun. 13, 2014, provisional application No. 60/364,214, filed on Mar. 11, 2002, provisional application No. 60/393,309, filed on Jul. 3, 2002, provisional application No. 60/421,001, filed on Oct. 25, 2002, provisional application No. 60/421,510, filed on Oct. 28, 2002, provisional application No. 60/427,833, filed on Nov. 21, 2002.

(51) Int. Cl.

| | | |
|---|---|---|
| *H01J 49/00* | (2006.01) | |
| *G01N 1/40* | (2006.01) | |
| *B01J 20/286* | (2006.01) | |
| *B01J 20/287* | (2006.01) | |
| *G01N 33/50* | (2006.01) | |
| *A61B 10/00* | (2006.01) | |
| *G01N 30/00* | (2006.01) | |
| *G01N 30/06* | (2006.01) | |
| *A61B 10/02* | (2006.01) | |

(52) U.S. Cl.
CPC .......... *G01N 33/50* (2013.01); *H01J 49/0031* (2013.01); *H01J 49/26* (2013.01); *A61B 10/0045* (2013.01); *A61B 10/02* (2013.01); *G01N 2030/009* (2013.01); *G01N 2030/062* (2013.01); *G01N 2560/00* (2013.01); *Y10T 428/2933* (2015.01)

(58) Field of Classification Search
CPC .... H01J 49/0409; H01J 49/16; H01J 49/0031; H01J 49/10; H01J 49/26; H01J 49/04
See application file for complete search history.

(56) References Cited

U.S. PATENT DOCUMENTS

| | | | |
|---|---|---|---|
| 4,616,652 A | 10/1986 | Simpson | |
| 5,047,437 A | 9/1991 | Cooke et al. | |
| 5,081,871 A * | 1/1992 | Glaser | A61B 5/083 422/84 |
| 5,120,510 A | 6/1992 | Gourley et al. | |
| 5,424,187 A | 6/1995 | Shor et al. | |
| 5,460,813 A | 10/1995 | Leung | |
| 5,464,395 A | 11/1995 | Faxon et al. | |
| 5,479,923 A | 1/1996 | Rantala | |
| 5,640,470 A | 6/1997 | Iyer et al. | |
| 5,691,206 A * | 11/1997 | Pawliszyn | B82Y 30/00 422/416 |
| 5,693,228 A | 12/1997 | Koehler et al. | |
| 5,808,300 A | 9/1998 | Caprioli | |
| 6,027,942 A * | 2/2000 | Hutchens | G01N 1/405 250/287 |
| 6,287,521 B1 | 9/2001 | Quay et al. | |
| 6,360,588 B1 | 3/2002 | Ross | |
| 6,555,813 B1 * | 4/2003 | Beecher | B01L 3/5085 250/281 |
| 6,558,958 B1 | 5/2003 | Pilevar | |
| 6,689,603 B2 | 2/2004 | Pompidou et al. | |
| 6,730,096 B2 | 5/2004 | Basta | |
| 6,743,180 B1 | 6/2004 | Van Bockel | |
| 6,808,937 B2 | 10/2004 | Ligler | |
| 6,871,556 B2 | 3/2005 | Andresen et al. | |
| 7,019,288 B2 | 3/2006 | Becker | |
| 7,125,580 B2 | 10/2006 | Miller et al. | |
| 7,151,167 B2 | 12/2006 | Gjerde et al. | |
| 7,211,189 B2 | 5/2007 | Jinno et al. | |
| 7,232,689 B2 | 6/2007 | Pawliszyn | |
| 7,259,019 B2 | 8/2007 | Pawliszyn et al. | |
| 7,384,794 B2 | 6/2008 | Pawliszyn | |
| 7,468,281 B2 | 12/2008 | Kallury et al. | |
| 7,537,803 B2 | 5/2009 | Wang et al. | |
| 7,605,003 B2 | 10/2009 | Chan | |
| 7,667,010 B2 | 2/2010 | Gierde et al. | |
| 8,008,064 B2 | 8/2011 | Pawliszyn et al. | |
| 8,148,161 B2 * | 4/2012 | Higgins | C08L 83/16 422/68.1 |
| 8,206,902 B2 | 6/2012 | Mitani et al. | |
| 8,362,219 B2 | 1/2013 | Gjerde et al. | |
| 8,399,055 B2 | 3/2013 | Bakry et al. | |
| 8,598,325 B2 | 12/2013 | Pawliszyn | |
| 9,108,217 B2 | 8/2015 | Hoerr et al. | |
| 9,502,226 B2 * | 11/2016 | Brown | H01J 49/049 |
| 2002/0034827 A1 | 3/2002 | Singh et al. | |
| 2003/0135195 A1 | 7/2003 | Jimenez et al. | |
| 2003/0180954 A1 | 9/2003 | Riviere et al. | |
| 2003/0183758 A1 | 10/2003 | Colburn et al. | |
| 2004/0005582 A1 | 1/2004 | Shipwash | |
| 2004/0171169 A1 | 9/2004 | Kallury et al. | |
| 2004/0191537 A1 | 9/2004 | Lubda et al. | |
| 2004/0224362 A1 | 11/2004 | Gjerde et al. | |
| 2004/0241721 A1 | 12/2004 | Gjerde et al. | |
| 2005/0032237 A1 | 2/2005 | Sandra et al. | |
| 2005/0112650 A1 * | 5/2005 | Chang | C08G 18/0814 435/6.12 |
| 2005/0133714 A1 * | 6/2005 | Vestal | H01J 49/0418 250/288 |
| 2005/0142033 A1 | 6/2005 | Glezer et al. | |
| 2008/0023630 A1 * | 1/2008 | Boschetti | H01J 49/0418 250/282 |
| 2008/0193772 A1 * | 8/2008 | Agroskin | G01N 1/2813 428/421 |
| 2009/0026122 A1 | 1/2009 | Pawliszyn et al. | |
| 2009/0301169 A1 * | 12/2009 | Higgins | C08L 83/16 73/23.2 |
| 2010/0130796 A1 * | 5/2010 | Combes | G01N 1/405 568/935 |
| 2010/0144049 A1 * | 6/2010 | Combes | G01N 1/405 436/106 |
| 2014/0017693 A1 * | 1/2014 | Mao | A61B 10/0045 435/6.12 |
| 2014/0346348 A1 * | 11/2014 | Krechmer | H01J 49/049 250/288 |
| 2015/0068280 A1 | 3/2015 | Ricoul | |
| 2015/0200083 A1 * | 7/2015 | Brown | H01J 49/049 250/282 |
| 2015/0231602 A1 | 8/2015 | Pawliszyn | |
| 2015/0318160 A1 * | 11/2015 | Pawliszyn | H01J 49/0409 250/282 |
| 2015/0364310 A1 * | 12/2015 | Musselman | H01J 49/16 250/282 |

FOREIGN PATENT DOCUMENTS

| | | |
|---|---|---|
| DE | 19905239 | 8/2000 |
| EP | 1618592 | 1/2006 |
| JP | 1164277 | 5/1999 |
| JP | 2009539114 A | 11/2009 |
| WO | 9115745 | 10/1991 |
| WO | 0068665 | 11/2000 |

(56) References Cited

FOREIGN PATENT DOCUMENTS

| WO | 2003075772 A3 | 9/2003 |
|---|---|---|
| WO | 2010008450 | 1/2010 |

OTHER PUBLICATIONS

Vail, Teresa M., Patrick R. Jones, and O. David Sparkman. "Rapid and unambiguous identification of melamine in contaminated pet food based on mass spectrometry with four degrees of confirmation." Journal of analytical toxicology 31, No. 6 (2007): 304-312.*
Smith et al., "Solid-Phase Microextraction as a Tool for Studying Volatile Compounds in Frog Skin", Chemistry and Ecology, 2000, vol. 17, pp. 215-225.
Whang et al., "Solid phase microextraction coupled to capillary electrophoresis", Anal. Commun., 1998, 35, pp. 353-356.
Yang et al., "Surface Modification and Blood Compatibility of Polyacrylonitrile Membrane with Immobilized Chitosan-Heparin Conjugate", Journal of Polymer Research 9: 2002, pp. 201-206, http://www.springerlink.com/content/m2878p248r41nk81/.
Zhang et al.. "Solid-Phase Microextraction", Analytical Chemistry, vol. 66, No. 17, Sep. 1, 1994, pp. 844-853.
Non-final Office Action dated Apr. 4, 2011 from corresponding U.S. Appl. No. 12/939,360.
English translation of Japanese Office Action dated Feb. 10, 2009 from corresponding Appl. No. 574050/2003.
Shirey, Robert E., "Optimization of Extraction Conditions and Fiber Selection for Semivolatile Analytes Using Solid-Phase Microextraction", Journal of Chromatographic Science, Jul. 2000, vol. 38, pp. 279-288.
Lambropoulou et al., "Validation of an SPME method, using PDMS, PA, PDMS-DVB, and CW-DVB SPME fiber coatings, for analysis of organophosphorus insecticides in natural waters", Anal Bioanal Chem, 2002. vol. 374, pp. 932-941.
Mullett et al., "Direct Determination of Benzodiazepines in Biological Fluids by Restricted-Access Solid-Phase Microextraction", Anal. Chem., 2002, vol, 74, pp. 1081-1087.
Mindrup, et al: "Improved Performance of SPME Fibers and Applications", SUPELCO 2001, Sigma-Aldrich Co. 2001, pp. 1-25.
Musteata, et al. "Biocompatible solid-phase microextraction coatings based on polyacrylonitrile and solid-phase extraction phases." Anal. Chem. 2007, vol. 79, pp. 6903-6911.
Musteata, Mihaela. "Biocompatible solid phase microextraction." Master Thesis, University of Waterloo, 2006. pp. i-xi and 1-70.
Wang, et al. "Surface confined ionic liquid as a stationary phase for HPLC., " Analyst 2006, vol. 131, pp. 1000-1005.
Non-final Office Action from U.S. Appl. No. 13/478,295 dated Feb. 11, 2015.
Restriction Requirement dated Oct. 9, 2014 from U.S. Appl. No. 13/478,295.
Boos et al. Alkyl-diol silica (ADS): restricted access precolumn packing for direct injection and coupled-column chromatography of biofluids. Fesenius J Anal Chem 1995, vol. 352, pp. 684-690.
Restriction Requirement dated Nov. 17, 2008 from corresponding U.S. Appl. No. 11/706,167.
Non-final Office Action dated Aug. 2, 2010 from corresponding U.S. Appl. No. 11/706,167.
Non-final Office Action dated Jan. 21, 2011 from corresponding U.S. Appl. No. 11/706,167.
Notice of Allowance dated Jun. 16, 2011 from corresponding U.S. Appl. No. 11/706,167.
Restriction Requirement dated Apr. 28, 2011 from corresponding U.S. Appl. No. 12/174,494.
Non-final Office Action dated Aug. 29, 2011 from corresponding U.S. Appl. No. 12/174,494.
Final Office Action dated Jan. 20, 2012 from corresponding U.S. Appl. No. 12/174,494.
Advisory Action dated Mar. 22, 2012 from corresponding U.S. Appl. No. 12/174,494.
Non-final Office Action dated Jun. 25, 2014 from corresponding U.S. Appl. No. 12/174,494.
Non-final Office Action dated Jun. 30, 2005 from corresponding U.S. Appl. No. 10/506,827.
Final Office Action dated Dec. 28, 2005 from corresponding U.S. Appl. No. 10/506,827.
Non-final Office Action dated May 30, 2006 from corresponding U.S. Appl. No. 10/506,827.
Final Office Action dated Oct. 26, 2006 from corresponding U.S. Appl. No. 10/506,827.
Non-final Office Action dated May 29, 2007 from corresponding U.S. Appl. No. 10/506,827.
Final Office Action dated Oct. 18, 2007 from corresponding U.S. Appl. No. 10/506,827.
Notice of Allowance dated Jan. 30, 2008 from corresponding U.S. Appl. No. 10/506,827.
Restriction Requirement dated Oct. 28, 2005 from corresponding U.S. Appl. No. 11/206,804.
Non-final Office Action dated Jan. 9, 2006 from corresponding U.S. Appl. No. 11/206,804.
Final Office Action dated Jul. 12, 2006 from corresponding U.S. Appl. No. 11/206,804.
Non-final Office Action dated Jan. 12, 2007 from corresponding U.S. Appl. No. 11/206,804.
Notice of Allowance dated May 16, 2007 from corresponding U.S. Appl. No. 11/206,804.
Restriction Requirement dated Dec. 1, 2005 from corresponding U.S. Appl. No. 11/208,933.
Non-final Office Action dated Mar. 27, 2006 from corresponding U.S. Appl. No. 11/208,933.
Non-final Office Action dated Aug. 9, 2006 from corresponding U.S. Appl. No. 11/208,933.
Final Office Action dated Jan. 3, 2007 from corresponding U.S. Appl. No. 11/208,933.
Notice of Allowance dated Feb. 20, 2007 from corresponding U.S. Appl. No. 11/208,933.
Non-final Office Action dated Apr. 1, 2011 from corresponding U.S. Appl. No. 12/938,876.
Notice of Allowance dated Jan. 11, 2012 from corresponding U.S. Appl. No. 12/938,876.
Notice of Allowance dated Nov. 10, 2011 from corresponding U.S. Appl. No. 12/939,360.
Restriction Requirement dated Jan. 22, 2013 from corresponding U.S. Appl. No. 13/412,122.
Non-final Office Action dated Apr. 8, 2013 from corresponding U.S. Appl. No. 13/412,122.
Final Office Action dated Jul. 25, 2013 from corresponding U.S. Appl. No. 13/412,122.
Notice of Allowance dated Sep. 13, 2013 from corresponding U.S. Appl. No. 1/412,122.
Communication from European Examining Division dated Oct. 23, 2006 from corresponding European Patent Application No. 03706179.3.
International Search Report and Written Opinion from corresponding PCT Application No. PCT/CA2015/050550 dated Aug. 27, 2015.
International Search Report and Written Opinion from corresponding PCT Application No. PCT/CA2015/050551 dated Aug. 27, 2015.
Deng et al.,"Strategies for coupling solid-phase microextraction with mass spectometry", Trends in Analytical Chemistry, 55, pp. 55-67, Mar. 2014.
R. M. Gonzalez-Rodriguez, B. Cancho-Grande, and J. Simal-Gandara, Multiresidue determination of 11 new fungicides in grapes and wines by liquid-liquid extraction/clean-up and programmable temperature vaporization injection with analyte protectants/gas chromatography/ion trap mass spectrometry, Journal of Chromatography A, 2009, vol. 1216, pp. 6033-6042.
K. Banerjee, D.P. Oulka, S. Dasgupta, S.B. Patil, S.H. Patil, R. Savant, and P.G. Adsule, Validation and uncertainty analysis of a multi-residue method for pesticides in grapes using ethyl acetate extraction and liquid chromatography-tandem mass spectrometry, Journal of Chromatography A, 2007, vol. 1173, 1-2, pp. 98-109.

(56) References Cited

OTHER PUBLICATIONS

V. Guillet, C. Fave, and M. Montury, Microwave/SPME method to quantify pesticides residues in tomato fruits, Journal of Environmental Science and Health Part B, 2009, vol. 44, pp. 415-422.

J. Oliva, A. Barba, N. Vela, F. Melendreras, and S. Navarro, Multiresidue method for the rapid determination of organophosphorous insecticides in grapes, must and wine, Journal of Chromatography A, 2000, vol. 882, pp. 213-220.

J. Oliva, S. Navarro, A. Barba, and G. Navarro, Determination of chlorpyrifos, penconazole, fenarimol, vinclozolin and metalaxyl in grapes, must and wine by on-line microextraction and gas chromatogaphy, Journal of Chromatography A, 1999, vol. 833, pp. 43-51.

A. J. A. Charlton, and A. Jones, Determination of imisazole and triazole fungicide residues in honeybees using gas chromatography-mass spectrometry, Journal of Chromatography A, 2007, 1141, pp. 117-122.

J. Zeng, J.i Chen, Z. Lin, W. Chen, X. Chen, and X. Wang, Development of polydimethylphenylsiloxane-coated fiber for solid-phase microextraction and its analytical application of qualitative and semi-quantitative of organochlorine and pyrethroid pesticides in vegetables, Analytica Chimica Acta, 2008, vol. 619, pp. 59-66.

M. Anastassiades, S. J. Lehotay, D. Stajnbaher, and F. J. Schenck, Fast and easy multiresidue method employing acetonitrile extraction/partitioning and "dispersive solid-phase extraction" for the determination of pesticide residues in produce. Journal of AOAC International, 2003, vol. 86, 2, pp. 412-431.

D. Steiniger, G. P.Lu, J. Butler, E. Phillips, and Y. Fintschenko, Determination of Multiresidue Pesticides in Green Tea by Using a Modified QuEChERS Extraction and Ion-Trap Gas Chromatography/Mass Spectrometry, Journal of AOAC International, 2010, vol. 93, 4, pp. 1169-1179.

S. C. Cunha, J. O. Fernandes, A. Alves, and M.B.P.P. Oliveira, Fast low-pressure gas chromatography-mass spectrometry method for the determination of multiple pesticides in grapes, must and wines, Journal of Chromatography A, 2009, vol. 1216, pp. 119-126.

Wong J, C.Y. Hao, K. Zhang, P. Yang, K. Banerjee, D. Hayward, I. Iftakhar, A. Schreiber, K. Tech, C. Sack C, M. Smoker, X.R. Chen, S.C. Utture, and D.P. Oulka, Development and Interlaboratory Validation of a QuEChERS-Based Liquid Chromatography-Tandem Mass Spectrometry Method for Multiresidue Pesticide Analysis, Journal of Agricultural and Food Chemistry, 2010, vol. 58, 10, pp. 5897-5903.

P. Paya, M. Anastassiades, D. Mack, I. Sigalova, B. Tasdelen, J. Oliva, and A. Barba, Analysis of pesticide residues using the Quick Easy Cheap Effective Rugged and Safe (QuEChERS) pesticide multiresidue method in combination with gas and liquid chromatography and tandem mass spectrometric detection. Analytical and Bioanalytical Chemistry, 2007, vol. 389, 6.

Pawliszyn and J. SPME Method Development. Solid Phase Microextraction: Theory and Practice, 1. New York : Wiley-VCH, 1997, pp. 97-139.

S. Risticevic, H. Lord, T. Gorecki, C. L. Arthur, and J. Pawliszyn, Protocol for solid phase microextraction method development, Nature Protocols, 2010, vol. 5, 1, pp. 122-139.

J. Schurek, T. Portoles, J. Hajslova, K. Riddellova, and F. Hernandez, Application of head-space solid-phase microextraction coupled to comprehensive two-dimensional gas chromatography-time-of-flight mass spectrometry for the determination of multiple pesticide residues in tea samples, Analytica Chimica Acta, 2008, vol. 611, 2, pp. 163-172.

D. A. Lambropoulou and T. A. Albanis, Headspace solid-phase microextraction in combination with gas chromatography-mass spectrometry for the rapid screening of organophosphorus insecticide residues in strawberries and cherries, Journal of Chromatography A, 2003, vol. 993, 1-2, pp. 197-203.

M. Natangelo, S. Tavazzi, and E. Benfenati, Evaluation of solid phase microextraction-gas chromatography in the analysis of some pesticides with different mass spectrometric techniques: Application to environmental waters and food samples, Analytical Letters, 2002, vol. 35, 2, pp. 327-338.

W. Chen, KF Poon and M. H. W. Lam, The application of solid phase microextraction in the analysis of organophosphorous pesticides in a food plant, Environmental Science & Technology, 1998, vol. 32, 23, pp. 3816-3820.

K. Fytianos, N. Raikos, G. Theodoridis, Z. Velinova, and H. Tsoukali.,Solid phase microextraction applied to the analysis of organophosphorous insecticides in fruits, Chemosphere, 2006, vol. 65, pp. 2090-2095.

A. Menezes Filho, F, N. Santos, and P. A. P. Pereira, Development, validation and application of a maethodology based on solid-phase micro extraction followed by gas chromatography coupled to mass spectrometry (SPME/GC-MS) for the determination of pesticides residues in mangoes, Talanta, 2010, vol. 81, pp. 346-354.

M. Volante, M. Pontello, L. Valoti, M. Cattaneo, M. Bianchi, and L. Colzani, Application of solid phase microextraction (SPME) to the analysis of pesticides residues in vegetables, Pest Management Science, 2000, vol. 56, pp. 618-636.

H. L. V. Capobiango and Z. L. Cardeal, A solid phase microextraction method for the chromatographic determination of organophosphorous pesticides in fish, water, potatoes, guava and coffee, Journal of Brazilian Chemical Society, 2005, vol. 16, 5, pp. 907-914.

C. G. Zambonin, M. Quinto, N. De Vietro, and F. Palmisano, Solid phase microextraction—gas chromatography mass spectrometry: A fast and simple screening method for the assessment of organophosphorous pesticides residues in wine and fruit juices. Food Chemistry, 2004, vol. 86, pp. 269-274.

C. G. Zambonin, A. Cilenti, F. Palmisano, Solid phase microextraction and gas chromatography-mass spectrometry for the rapid screening of triazole residues in wine and strawberries, Journal of Chromatography A, 2002, vol. 967, pp. 255-260.

A. Aguinaga, N, Campillo, P. Vinas, and M. Hernadez-Cordoba, Solid phase microextraction coupled to gas chromatography-mass spectrometry for the analysis of famoxadone in wines, fruits and vegetables, Spectroscopy Letters, 2009, vol. 42, pp. 320-326.

R. Hu, B. Hennion, L. Urruty, and M. Montury, Solid phase microextraction of pesticide residues from strawberries, Food Additives and Contaminants, 1999, vol. 16, 3, pp. 111-117.

P. Vinas, N. Campillo, N. Martinez-Castillo, and M. Hernandez-Cordoba, Method development and validation for strobilurin fungicides in baby foods by solid phase microextraction gas chromatography-mass spectrometry, Journal of Chromatography A, 2009, vol. 1216, pp. 140-146.

K. Ridgway, S. P. D. Lalljie, and R. M. Smith, Sample preparation techniques for the determination of trace residues and contaminants in food, Journal of Chromatography A, 2007, vol. 1153, pp. 36-53.

F. Augusto, E. Carasek. R. G. C. Silva, S. R. Rivellino, A. D. Batista, and E. Martendal, New sorbents for extraction and microextraction techniques, Journal of Chromatography A, 2010, vol. 1217, pp. 2533-2542.

L. Cai, S. Gong, M. Chen, and C. Wu, Vinyl crown ether as a novel radical crosslinked sol-gel SPME fiber for determination of organousphosphorous pesticides in food samples, Analytica Chimica Acta, 2006, vol. 559, pp. 89-96.

D. Djozan, M. Mahkam, and B. Ebrahimi, Preparation and biding study of solid phase microextraction fiber on the basis of ametryn-imprinted polymer—Application to the selective extraction of persistent triazine herbicides in tap water, rice, maize and onion, Journal of Chromatography A, 2009, vol. 1216, pp. 2211-2219.

E. Turiel, J. L. Tadeo, and A. Martin-Esteban, Molecularly imprinted polymeric fibers for solid phase microextraction. Analytical Chemistry, 2007, vol. 79, pp. 3099-3104.

C. Dietz, J. Sanz, and C. Camara, Recent developments in solid phase microextraction coatings and related techniques, Journal of Chromatography A, 2006, vol. 1103, pp. 183-192.

J. Beltran, F.J. Lopez, and F. Hernandez, Solid-phase microextraction in pesticide residue analysis, Journal of Chromatography A, 2000, vol. 885, pp. 389-404.

(56) References Cited

OTHER PUBLICATIONS

A. Jahnke and P. Mayer, Do complex matrices modify the sorptive properties of polydimethylsiloxane (PDMS) for nonpolar organic chemicals, Journal of Chromatography A, 2010, vol. 1217, 29, pp. 4765-4770.

D. Vuckovic, R. Shirey, Y. Chen, L. Sidisky, C. Aurand, K. Stenerson, and J. Pawliszyn, In vitro evaluation of new biocompatible coatings for solid-phase microextraction: Implications for drug analysis and in vivo sampling applicatons, Analytica Chimica Acta, 2009, vol. 638, pp. 175-185.

L. S De Jager, G. A. Perfetti, and G. W. Diachenko, Analysis of tetramethylene disulfotetramine in foods using solid-phase microextraction-gas chromatography-mass spectrometry, Journal of Chromatography A, 2008, vol. 1192, pp. 36-40.

A. L. Simplicio and L. V. Boas, Validation of a solid-phase microextraction method for the determination of organophosphorous pesticides in fruits and fruit juice, Journal of Chromatography A, 1999, vol. 833, pp. 35-42.

A. Kloskowski and M. Pilarczyk, Membrane solid-phase microextraction—A new concept in sorbent preparation, Analytical Chemistry, 2009, vol. 81, pp. 7363-7367.

Frérot et al., "Solid-Phase Microextraction (SPME): A New Tool in Pheromone Identification in Lepidoptera", J. High Resolut. Chromatogr., 1997, vol. 20, pp. 340-342.

Heinze, "Ultramicroelectrodes in Electrochemistry", Angew. Chem. Int. Ed. Engl., 1993, 32, pp. 1268-1288.

Jackson et al., "Mass spectrometry for genotyping: an emerging tool for molecular medicine", Molecular Medicine Today, Jul. 2000, vol. 6, pp. 271-276.

Lavaud et al., "Optimal anticoagulation strategy in haemodialysis with heparin-coated polyacrylonitrile membrane", Nephrology Dialysis Transplantation, 2003, 18, pp. 2097-2104, available at http://ndt.oxfordjournals.org/cgi/content/abstract/18/10/2097V.

Lord et al., "Development and Evaluation of a Solid-Phase Microextraction Probe for in Vivo Pharmacokinetic Studies", Anal. Chem. Oct. 1, 2003, vol. 75, No. 19, pp. 5103-5115.

Moneti et al., "Solid-phase Microextraction of Insect Epicuticular Hydrocarbons for Gas Chromatographic/Mass Spectrometric Analysis", Rapid Communications in Mass Spectrometry, vol. II, 1997 pp. 857-862.

Namera et al., "Analysis of anatoxin-a in aqueous samples of solid-phase microextraction coupled to high-performance liquid chromatography with fluorescence detection and on-fiber derivatization", Journal of Chromatography A, 963, 2002, pp. 295-302.

Nie et al., "Preparation and Characterization of polyacrylonitrile-based membranes: Effects of internal coagulant on poly (acrylonitrile-co-maleic acid) ultrafiltration hollow fiber membranes", Desalination 160 (2004) pp. 43-50.

Communication from European Examining Division dated Jan. 24, 2007 from corresponding European Patent Application No. 03706179.3.

Communication from European Examining Division dated Dec. 17, 2007 from corresponding European Patent Application No. 03706179.3.

Communication from European Examining Division dated Apr. 29, 2008 from corresponding European Patent Application No. 03706179.3.

Intention to Grant from European Examining Division dated Aug. 19, 2008 from corresponding European Patent Application No. 03706179.3.

Canadian Patent Application No. 2945845, Office Action dated May 5, 2017.

Moder et al., Determination of urinary acylcarnitines by ESI-MS couple with solid-phase microextraction (SPME). J. Mass Spectrometry, Jul. 22, 1997, vol. 32, pp. 1195-1204.

U.S. Appl. No. 14/839,529, Final Office Action dated Jun. 12, 2017.

Alpendurada, "Solid-Phase Microextraction: A Promising Technique for Sample Preparation in Environmental Analysis", Journal of Chromatography A, Aug. 2011, vol. 889 (1-2), pp. 3-14.

Hu et al., "Solid-phase Microextraction of Phenol Compounds Using a Fused-Silica Fiber Coated with beta-Cyclodextrin-bonded Silica Particles", Analytical Sciences, Apr. 2004, vol. 20, pp. 667-671.

International Patent Application No. PCT/CA2003/000311, Search Report dated Oct. 10, 2003.

Sigma-Aldrich, SPME Sample Prep Made Easy, How to Choose the Proper SPME Fiber, Newsletter, Sigma-Aldrich, Supelco, Supelco Park, Bellefonte, PA 16823-0048, Fall 1999, 4 pages.

Kataoka et al., "Applications of Solid-Phase Microextraction in Food Analysis", Journal of Chromatography A, Jun. 2000, vol. 880 (1-2), pp. 35-62.

Louch et al., "Dynamics of Organic Compound Extraction from Water Using Liquid-Coated Fused Silica Fibers", Anal. Chem. vol. 64, May 1992, 1187-1199.

Martos et al., "Calibration of Solid Phase Microextraction for Air Analyses Based on Physical Chemical Properties of the Coating," Anal. Chem. vol. 69, No. 2, Jan. 1997, 206-215.

U.S. Appl. No. 14/492,411 Office Action dated Feb. 16, 2016.

U.S. Appl. No. 14/738,688 Office Action dated Nov. 10, 2016.

Poerschmann et al., "Solid Phase Microextraction for Determining the Distribution of Chemicals in Aqueous Matrices", Journal of Analytical Chemistry, Feb. 1997, vol. 69 (4), pp. 597-600.

U.S. Appl. No. 14/839,529 Restriction Requirement dated Oct. 4, 2016.

Reubsaet et al., "Determination of Benzodiazepines in Human Urine and Plasma with Solvent Modified Solid Phase Micro Extraction and Gas Chromatography; Rationalisation of Method Development Using Experimental Design Strategies," Journal of Pharmaceutical and Biomedical Analysis, Dec. 1998, vol. 18 (4-5), pp. 667-680.

Furlong et al., "Routine Determination of Sulfonylurea, Imidazolinone, and Sulfonamide Herbicides at Nanogram-Per-Liter Concentration by Solid-Phase Extraction and Liquid Chromatography/Mass Spectrometry," The Science of the Total Environment, Apr. 2000, vol. 248 (2-3), pp. 135-146.

U.S. Appl. No. 14/705,238 Restriction Requirement dated May 19, 2016.

U.S. Appl. No. 14/705,238 Office Action dated Sep. 7, 2016.

International Preliminary Report on Patentability issued on the corresponding International application No. PCT/CA2015/050551, dated Dec. 22, 2016.

International application No. PCT/CA2015/050550 International Preliminary Report on Patentability dated Dec. 22, 2016.

Chen et al., "Solid Phase Microextraction Coupled to High-Performance Liquid Chromatography," Analytical Chemistry, Aug. 1995, vol. 67 (15), pp. 2530-2533.

U.S. Appl. No. 14/839,529, Office Action dated Jan. 26, 2017.

Chipuk et al., "The Influence of Material and Mesh Characteristics on Transmission Mode Desorption Electrospray Ionization," Journal of the American Society for Mass Spectrometry, Apr. 2009, Published Online on Dec. 3, 2008, vol. 20 (4), pp. 584-592.

Chipuk et al., "Transmission Mode Desorption Electrospray Ionization," Journal of the American Society for Mass Spectrometry, Nov. 2008, Published Online on Jul. 2008, vol. 19 (11), pp. 1612-1620.

Gomez-Rios et al., "Solid Phase Microextraction (SPME)-Transmission Mode (TM) Pushes Down Detection Limits in Direct Analysis in Real Time (DART)," Chemical Communications, Accepted Aug. 2014, vol. 50, pp. 12937-12940.

Mirnaghi et al., "Optimization of the Coating Procedure for a High-Throughput 96-Blade Solid Phase Microextraction System Coupled with LC-MS/MS for Analysis of Complex Samples," Analytical Chemistry, Jun. 2011, vol. 83 (15), pp. 5018-6025.

Perez et al., "Transmission-Mode Direct Analysis in Real Time and Desorption Electrospray Ionization Mass Spectrometry of Insecticide-Treated Bednets for Malaria Control," Analyst, Feb. 2010, vol. 135, pp. 712-719.

(56) References Cited

OTHER PUBLICATIONS

Rodriguez-Lafuente et al., "Determination of Cocaine and Methadone in Urine Samples by Thin-Film Solid-Phase Microextraction and Direct Analysis in Real Time (DART) Coupled With Tandem Mass Spectrometry," Analytical and Bioanalytical Chemistry, Dec. 2013, Published Online on May 19, 2013, vol. 405 (30), pp. 9723-9727.

Japanese Patent Application No. 2017-517155, Office Action dated Nov. 14, 2017—with English Translation.

* cited by examiner

PROBE FOR EXTRACTION OF MOLECULES OF INTEREST FROM A SAMPLE

CROSS REFERENCE TO RELATED APPLICATIONS

This application is a continuation-in-part of U.S. patent application Ser. No. 14/705,238, filed May 6, 2015; which is a continuation of U.S. patent application Ser. No. 13/478,295, filed May 23, 2012; which is a divisional application of U.S. patent application Ser. No. 12/174,494, filed Jul. 16, 2008; which was a continuation-in-part of U.S. patent application Ser. No. 11/706,167 filed Feb. 15, 2007 (now U.S. Pat. No. 8,008,064); which is a continuation of U.S. patent application Ser. No. 11/208,933 filed Aug. 23, 2005 (now U.S. Pat. No. 7,232,689); which is a continuation-in-part of U.S. patent application Ser. No. 10/506,827 filed Sep. 7, 2004 (now U.S. Pat. No. 7,384,794) which is derived from International Patent Application PCT/CA2003/0000311. Further, this application is entitled to the benefit of, and claims priority to, U.S. Patent Application No. 60/364,214, filed Mar. 11, 2002; U.S. Patent Application No. 60/393,309, filed Jul. 3, 2002; U.S. Patent Application No. 60/421,001, filed Oct. 25, 2002; U.S. Patent Application No. 60/421,510, filed Oct. 28, 2002; and U.S. Patent Application No. 60/427,833 filed Nov. 21, 2002. This application also claims the benefit of priority of U.S. Provisional Patent Application No. 61/997,937 filed Jun. 13, 2014. The entirety of each document is incorporated herein by reference.

FIELD

The present disclosure relates to methods and devices for mass spectrometry analysis of molecules of interest present in a sample.

BACKGROUND

Mass spectrometry coupled to liquid chromatography and gas chromatography are undeniably the most important and regularly used analytical tools to detect, identify and quantitate molecules around the world. However, extensive, expensive and elaborate sample-preparation/separation steps are commonly required to analyze complex sample (e.g. food matrices, whole blood, plasma, saliva, or urine) by mass spectrometry. In the last decade, ambient ionization methods have changed the way samples are analyzed by mass spectrometry. Several techniques such direct analysis in real-time (DART), desorption electrospray ionization (DESI), and paper spray (PS) have provided scientific community with key tools for screening, pass/fail analysis, fingerprinting, and native sample imagining applications. As a matter of fact, most ambient mass spectrometry (AMS) approaches seek for no sample preparation. Hence, the scientific communities, usually trained on standard sample preparation/separation methods, have numerous enquiries regarding the ability of AMS techniques to perform accurately and fast quantitative analysis. For instance, these methods are usually non-suitable to achieve trace analysis (e.g. low pg $mL^{-1}$) in complex matrices circumventing all sample preparation steps. In addition, it is not always true that the entire analysis can be performed in exceptionally short periods of time (i.e. ≤1 minute). Generally, given that there is no sample pre-treatment, the analyst should concede both: the analysis time (e.g. time required to dry the sample onto the paper substrate) and the linear dynamic range (i.e. diminished sensitivity by ion suppression). Consequently, improvements are required to obtain better in situ analyte quantitation. Therefore, rather than no sample treatment, minimal sample preparation could result in lower detection limits and more efficient analysis. A green-chemistry technique capable of combining sampling, sample preparation, analyte enrichment and ionization on a single device is an unmet need for the scientific community.

Thus, these modern techniques offer an attractive solution for real-time and on-site analysis of complex samples. Among this family of techniques, desorption electrospray ionization (DESI) and direct analysis in real time (DART) have become the most established. In essence, these techniques "wipe-off" analytes from the samples by exposing their surfaces to an ionizing medium which is essentially a gas or an aerosol. Although these techniques have represented a revolution in environmental, forensic, clinical and food applications, its operation generally requires sophisticated and costly equipment (e.g. pneumatic assistance, continuous flow of a solvent or a gas, and electronics to control sample positioning).

SUMMARY

To address at least one of the shortfalls and needs described above, an extractive device is disclosed. The extractive device includes a substrate coated with an extraction phase that sorbs a molecule of interest from a matrix. The extraction phase may include: a polymer that absorbs a molecule of interest from a matrix, or a polymer and solid phase microextraction (SPME) particles having pores dimensioned to adsorb a molecule of interest from a matrix. Solid Phase Microextraction (SPME) may be performed using either a polymer or solid particles.

The substrate is preferably a mesh substrate where the mesh substrate has a sufficiently open structure to allow fluid to flow through the mesh substrate. Exemplary devices include a solid substrate connected to the mesh substrate to provide stability to the coated mesh substrate.

The extractive device can be coupled as a transmission mode (TM) substrate to a thermal or solvent based desorption source of a mass spectrometer. The thermal or solvent based desorption source may use a heated gas with electronic excited-state species to desorb a molecule sorbed on the surface of the SPME device.

One thermal based desorption source that may be used with extractive devices according to the present disclosure is direct analysis in real time (DART). DART applies an electric potential to a gas, for example nitrogen, neon or helium, to generate a glow discharge creates a plasma containing ionized gas, electrons and excited state atoms or molecules (which are referred to as metastable species). A potential is applied to remove charged particles, leaving the metastable species. The metastable species are heated and used to desorb the molecule sorbed on the surface of the extractive device.

Alternative thermal or solvent based desorption sources that may be used with SPME devices according to the present disclosure include devices that ionize molecules using, for example: Plasma Assisted Desorption/Ionization (PADI), Dielectric Barrier Discharge Ionization (DBDI or DCBI), Desorption Atmospheric Pressure Chemical Ionization (DAPCI), Desorption Sonic Spray Ionization (DeSSI), Desorption Atmospheric Pressure Photoionization (DAPPI), Flowing Atmospheric-Pressure Afterglow (FAPA), Desorption Electrospray Ionization (DESI), atmospheric laser desorption ionization, Corona discharge, Inductively Coupled Plasma (ICP), glow discharge.

The present disclosure also generally relates to systems and methods to extract or enrich analytes of interest present in a sample, and subsequently generate ions for mass spectrometry. The present disclosure provides a system that may collect, enrich and transfer chemicals of interest from the matrix to the mass spectrometer independently of its sample dimensions or complexity. The system disclosed herein, when the extractive phase includes a polymer and solid phase microextraction (SPME) particles, may be referred to as solid phase microextraction-transmission mode (SPME-TM) as it can be used without further modification as a transmission mode (TM) substrate for desorbing a molecule that is sorbed on the surface of the SPME device using a thermal or solvent based desorption technique. The thermal or solvent based desorption technique may use, for example, a plasma or a non-plasma source to desorb the molecule.

The expression "analyte of interest" and "compound of interest" should be understood to be synonymous. In some examples, a compound of interest may be a "chemical of interest" or a "molecule of interest". A molecule of interest may be a small molecule. A small molecule can be hydrophobic or hydrophilic and preferably has a molecular weigh that less than 10,000 atomic mass units. The molecule can be, for example, a drug or a biomarker. A biomarker is a physiological substance that when present in abnormal amounts may indicate the presence of a disease.

In certain aspects, the present disclosure provides systems and methods for ion generation using a solid coated substrate that substantially prevents the contamination and/or damage of the mass spectrometer analyzer because the system or method extracts at least a portion of the analytes of interest while discarding matrix components such as proteins, carbohydrates, salts and detergents, for example in a rinsing step.

In certain aspects, devices and methods disclosed herein comprise a mesh substrate coated on the strands with an extractive coating that includes a polymer, preferably a biocompatible polymer, and solid phase microextraction (SPME) particles having pores dimensioned to adsorb a molecule of interest from a matrix. The polymer covers the SPME particles, but still allows at least some of the analytes of interest present in the matrix to be adsorbed by the SPME particles. The polymer may be considered to suspend the SPME particles therein, or adhere the SPME particles to the mesh substrate, or both.

According the present disclosure, a mesh substrate is a substrate that allows a fluid to flow through the substrate. A mesh substrate may comprise a plurality of connected or impregnated wires, filaments or strings, for example in a grid. When the mesh substrate comprises a plurality of connected or impregnated wires, filaments or strings, the wires, filaments or strings may have a diameter from micrometer to millimeters. Preferably, the diameter of the wires, filaments or strings is from 50 micrometers to 0.5 millimeters. More preferably, the diameter is about 94 micrometers. The number of wires, filaments or strings per square inch may be from 20×20 to 80×80. In preferred examples, the number of wires, filaments or strings per square inch is 74×74. The mesh substrate may have an open area of about 20% to about 70%. Mesh substrates with a greater percent open area are preferable since they interfere less with fluid flowing through the mesh and, accordingly, provide less variable results when the mesh is being desorbed. Preferred mesh substrates have an open area of about 50% to about 60%.

The mesh substrate, such as when the mesh substrate comprises wires, filaments or strings, may include a metal, or a metal alloy, or a polymer substrate. Mesh substrates that conduct heat are preferred since the conducted heat increases the desorption of sorbed analytes. In preferred examples, the substrate is: stainless steel, nitinol, nickel, titanium, aluminum, brass, iron, bronze, or polybutylene terephthalate. Mesh substrates may also be formed from materials that can be used in 3D printing. When the substrate is 3D printed, it is printed using a material suitable for 3D printing, such as: acrylonitrile butadiene styrene (ABS), polycarbonate-ISO (PC-ISO), polycarbonate (PC), polycarbonate-acrylonitrile butadiene styrene (PC-ABS), polyetherimide (such as ULTEM™), or polyphenylsulfone (PPSF). It is particularly beneficial to use a metal with shape memory properties (such as nitinol) when the coated mesh substrate is used in a method that includes insertion into a tissue or agitation at high speeds. Using a metal with shape memory properties in such methods enables the substrate to maintain, for example, a flat shape. In other examples, the polymer substrate may include a material synthesized from one or more reagents selected from the group consisting of styrene, propylene, carbonate, ethylene, acrylonitrile, butadiene, vinyl chloride, vinyl fluoride, ethylene terephthalate, terephthalate, dimethyl terephthalate, bis-beta-terephthalate, naphthalene dicarboxylic acid, 4-hydroxybenzoic acid, 6-hyderoxynaphthalene-2-carboxylic acid, mono ethylene glycol (1,2 ethanediol), cyclohexylene-dimethanol, 1,4-butanediol, 1,3-butanediol, polyester, cyclohexane dimethanol, terephthalic acid, isophthalic acid, methylamine, ethylamine, ethanolamine, dimethylamine, hexamthylaminediamine (hexane-1,6-diamine), pentamethylenediamine, methylethanolamine, trimethylamine, aziridine, piperidine, N-methylpiperideine, anhydrous formaldehyde, phenol, bisphenol A, cyclohexanone, trioxane, dioxolane, ethylene oxide, adipoyl chloride, adipic, adipic acid (hexanedioic acid), sebacic acid, glycolic acid, lactide, caprolactone, aminocaproic acid and blends of two or more materials synthesized from the polymerization of these reagents.

The solid phase microextraction (SPME) particles having pores dimensioned to adsorb a molecule of interest from a matrix may be, for example: C-18/silica, RP-amide/silica, or HS-F5/silica. C-18/silica particles would be understood by one of skill in the art to comprise silica particles derivatized with a hydrophobic phase, the hydrophobic bonded phase comprising octadecyl. For RP-amide-silica particles, the bonded phase comprises palmitamido-propyl. For HS-F5-silica particles, the bonded phase comprises pentafluorophenyl-propyl. It would be understood by a person of skill in the art that appropriate coatings can be formed with other extractive particles, and particularly with any extractive particles currently used in solid phase extraction or affinity chromatography (e.g. liquid chromatography), depending on the nature of the compound being extracted, in a similar manner than affinity chromatography relies on different particles for separating various compounds. For example, other particles could include such particles as: normal-phase silica, C1/silica, C4/silica, C6/silica, C8/silica, C30/silica, phenyl/silica, cyano/silica, diol/silica, ionic liquid/silica, molecular imprinted polymer particles, hydrophilic-lipophilic-balanced (HLB) particles, carboxen 1006 or divinylbenzene. Phenyl/silica particles would be understood by one of skill in the art to comprise silica particles having phenyl groups chemically bonded thereto. Mixtures of particles can also be used in the coatings. The particles can be inorganic (e.g. silica), organic (e.g. carboxen or divinylbenzene) or inorganic/organic hybrid (e.g. silica and organic polymer).

The particles can be about 0.2 to about 100 μm particles. Preferably, the particles are about 0.2 to about 60 μm particles. More preferably, the particles are about 0.2 to about 30 μm particles. Even more preferably, the particles can be about 0.2 to about 5 μm particles. The particles can be spherical. The pore size diameter can be about 10 to about 200 Å. Preferably, the pore size can be about 100 to about 180 Å. The surface area can be about 200 $m^2$/g to about 800 $m^2$/g. Preferably, the surface area can be about 200 $m^2$/g to about 300 $m^2$/g.

The biocompatible polymer may comprise, for example, polyacrylonitrile (PAN), polyethylene glycol, polypyrrole, derivatised cellulose, polysulfone, or polyamide. Furthermore, a person of skill in the art would understand that other biocompatible polymers could be used as glue or support.

In particular examples, the coatings can be prepared by covering a mesh with a suspension of various extractive particles (for example: C-18/silica, HLB, RP-amide/silica, or HS-F5/silica) in a polyacrylonitrile (PAN), polyethylene glycol, polypyrrole, derivatised cellulose, polysulfone, or polyamide solution.

Coated mesh substrates according to the present disclosure are preferably produced using methods that generate homogeneous coatings across the mesh substrate. Coated mesh substrates according to the present disclosure may be produced through a batch-coating process. In a batch-coating process, the biocompatible coating is preferably PAN or Polyethylene glycol (PEG). In the exemplary process, the extractive particles can be C-18, RP-amide, HS-F5 silica particles or any other particle listed above. Mixtures of particles can be used. When the particles are silica particles and the biocompatible coating is PAN, the ratio of PAN/silica can be between 0.05 and 0.25 wt/wt. The preferred ratio of PAN/silica is between 0.10 and 0.18 wt/wt. The ratio is based on the bare weight of silica and adjusted to the phase loading on the silica particles. The biocompatible coating may be dissolved in a solvent. The PAN/solvent solution can be between 0.5% and 2% PAN (w/w). Preferably, the PAN/solvent solution is between about 0.8% and about 1.2% PAN (w/w). More preferably, the PAN/solvent solution is about 1% PAN/solvent (w/w). The solvent can be any solvent known to one of skill in the art that dissolves PAN, for example: dimethylformamide (DMF), dimethyl sulfoxide, NaSCN, $Ca(CNS)_2$, ethylene carbonate or mixtures thereof. More preferably, the solvent can be DMF. The surface of the mesh substrate may be etched before the coating is applied. Applying a coating on an etched surface provides better attachment of the coating particles to the surface. A mesh substrate, such as a metal mesh substrate, may be etched with nitric acid, hydrofluoric acid, sulphuric acid, or hydrochloric acid. Preferably, the acid used to etched the mesh substrate is hydrochloric acid. Hydrochloric acid used for the etching process may be used in the range of about 18 to about 37% (vol/vol). Preferably, the etching process is achieved using 37% (vol/vol) hydrochloric acid. The mesh substrate may be etched for about 2 to about 8 minutes. Preferably, the etching time is about 5 minutes.

The solids substrates may be coated with one layer, or more than one layers, of coating. After applying a layer of coating, the coated substrate is preferably passed through a flow of an inert gas to remove most excess coating solution that remains accumulated in the mesh openings. High-purity gases such as nitrogen, argon, or helium can be used to remove the excess coating solution. Preferably, high purity nitrogen is used to remove the excess coating solution. The flow of gas used to remove the excess coating solution may be from about 0.5 to about 3 L/min. Preferably, the flow of the gas is from about 0.5 to about 1.5 L/min. Removing excess coating solution from the mesh openings improves the homogeneity of the coatings across the mesh substrate and increases the reliability of ion transmission during the desorption and ionization step.

After the excess coating solution is removed from the mesh substrate, the coated mesh substrate can be passed through a heater at an elevated temperature to remove at least a portion of the solvent. The elevated temperature can be from about 120° C. to about 300° C. Preferably, the elevated temperature is from about 120° C. to about 150° C. A person of skill in the art would readily understand that PAN is fully polymerized when it is dissolved in the solvent and as long as the solvent is fully evaporated, or at least substantially fully evaporated, the mesh substrate is properly coated. As such, any means known to a person of skill in the art to remove the solvent can be used to dry the coated substrates.

As an SPME device, the device and method described herein simultaneously isolates and enriches the analytes present in a sample, such as a fluid. In addition, since the coating can be adjusted towards analytes of interest, reduction of undesirable artefacts that might provide ion suppression or enhancement may be achieved.

When the coated mesh substrate is used as a transmission mode substrate for DART, the coated mesh is positioned between the DART nozzle and the MS inlet. In this position, most of the analytes sorbed on the coated mesh substrate are desorbed and ionized by a metastable gas stream flowing through the mesh substrate, and the ionized analytes are transferred to the mass spectrometer. Preferably, the coated mesh substrate is positioned such that the mesh substrate, the DART nozzle and the MS inlet are all coaxial to one-another, at 0° angle. The metastable gas stream flows through the mesh, desorbing and ionizing most of the compounds sorbed on the surface of the coating particles. Ionized analytes are transported into an atmospheric pressure interface (API) and analyzed by tandem mass spectrometry. In particular examples, carry over below 5% from one experiment to the next can be attained when desorbing analytes using DART.

In some aspects, devices and methods disclosed herein combine sampling, sample preparation and analyte isolation or enrichment with the accurate positioning of the analytes needed for direct analysis in real time (DART). The desorption of the analytes sorbed on the coated mesh substrate can be performed by scanning the surface of the coated mesh substrate using the DART nozzle. Scanning the surface of the coated mesh substrate allows the mass spectrometer to measure changes in the distribution of the analytes across the surface of the coated mesh substrate. This is possible when the size of the source nozzle is significantly smaller than the size of the mesh substrate, for example when the source nozzle is micrometers in diameter.

Device and methods disclosed herein may allow for quick analysis of chemicals in complex matrices, such as biofluids or food matrices, without compromising sample clean-up needed for mass spectrometry analysis. Devices and methods of the present disclosure may allow for the quick analysis of water-based salt solutions, food matrices, plasma and urine.

Devices and methods disclosed herein may be used to isolate or enrich analytes of interest by immersing the device into a sample or by spotting a fluid sample onto the coated mesh substrate. For example, a droplet or droplets comprising a biological fluid (for example blood or lysed cells) may be placed on the coated solid mesh substrate. Analytes of interest are transported from the sample to the coated mesh by the interaction between the coating on the mesh substrate and the sample. When the sample is a fluid, the sample can flow through the mesh openings, thereby improving the interaction between the sample and the SPME particles and polymer coating the mesh substrate. The interaction between the coated mesh and the sample can be from a few seconds to several hours. A coated mesh substrate according to the present disclosure may be used to perform extraction and enrichment of analytes of interest from samples by agitating the sample at high speed (e.g. vortex agitation). Increasing the rate of agitation may increase the rate of extraction and enrichment. The extraction or enrichment may be performed from samples enclosed in a small container, where the volume of the container may be, for example, from a few microliters to a few liters. The device may be rinsed one or more times to remove artefacts (e.g. fibers, proteins, cells, particulate matter, detergents, salts) that may be adhered to the coating surface without desorbing the analytes previously extracted or enriched. The coated mesh substrate may be rinsed using a solvent that does not desorb the analyte from the coating. In particular examples, the solvent may be water, such as Liquid chromatography/mass spectrometry (LC/MS) grade water. The coated mesh substrate may be rinsed a sufficient number of times to substantially eliminate artefacts. If a solvent is used that does not desorb the analyte, the coated substrate can be rinsed multiple times with substantially no loss of the extracted analyte from the coating.

In order to account for variations among mass spectrometry devices and/or variations among samples during extraction and/or ionization, an internal standard may be included in the coating layer, or included in the sample prior to the extraction or enrichment process. The internal standard can be preloaded in the coating layer prior to the extraction of the analytes of interest. Alternatively, internal standards may be included in both the coating prior to the extraction of the analytes and in the sample prior to the extraction.

Devices and methods of the present disclosure can be used to perform extraction or enrichment of analytes of interest from a sample. The sample may be a biological fluid or tissue. The biological fluid can be whole blood, plasma, serum, cerebrospinal fluid, peritoneal fluid, saliva or urine. The extraction or enrichment of analytes from different fluids or tissues may be independent of the sample characteristics (volume, complexity, and viscosity).

Preferred devices according to the present disclosure include a coated mesh substrate, such as discussed above, and a solid support for the mesh substrate to provide stability to the coated mesh substrate when the coated mesh substrate is being desorbed or agitated during extraction and enrichment, such as when the coated mesh substrate is being desorbed by flowing a hot metastable gas or a heated gas through the mesh. The solid support may reduce the chance that the mesh substrate is deformed or damaged. In some examples, the stability is provided by a mesh-blade configuration, such as described in greater detail below.

A holder may be provided to hold the solid support and position the coated mesh substrate in front of a ceramic ion-transfer tube in order to transmit ionized molecules to the mass spectrometer. The holder allows the coated mesh substrate to be replaced, quickly and easily, between experiments. The holder is preferably constructed using a chemically inert material, e.g. Teflon, poly(methyl methacrylate), or a 3D printed material. The holder may be installed on a customized 2D-translation stage that adjusts the position with high precision on each dimension. By placing different portions of the device in front of the transfer tube, the holder can facilitate characterization of analyte distribution on the surface to the coated mesh substrate. For example, desorbing of analytes sorbed on the coated mesh substrate may performed across the mesh substrate to facilitate characterization of a gradient in distribution of analytes along the mesh substrate. Up to twelve coated mesh substrates held in their respective solid supports can be placed into a holder, enabling rapid parallel sampling and/or sample-preparation. The holder allows easy and quick replacement of the SPME-TM devices. Arranging eight of these holders allows for a concurrent and automated analysis of up to 96 samples in a single run in multi-well-plate format.

Coating thickness should be as thin as possible, but thick enough to include at least one layer of particles. In preferred examples, the coating includes one or two layers of particles. In particularly preferred examples, the coating includes only a single layer of particles. In some examples, the coating is from about 0.2 μm to about 100 μm. In some examples, the coating is from about 1.9 μm to about 20 μm. Thinner coatings, and coatings with fewer numbers of layers of particles, result in more efficient mass transfer of the analytes (faster extraction or enrichment), but also more effective desorption/ionization when a desorption fluid is applied. Octadecyl silane or HLB particles with particle size of 1.9 μm or 5 μm may be used.

The coated mesh substrate may be reused after a cleaning step. Where the coating corresponds to octadecyl silane particles, the cleaning step may include agitation of the probe in a mixture of isopropanol, acetonitrile and methanol. Cleaning step may be changed according to the chemistry of the coating and its affinity towards the analyte of interest. In cases in which there is a vast variability in sample concentration among samples (e.g. low ppt to high ppb or even ppm levels), a coated mesh substrate may be used only once to reduce false positives.

DETAILED DESCRIPTION

Figure 1:
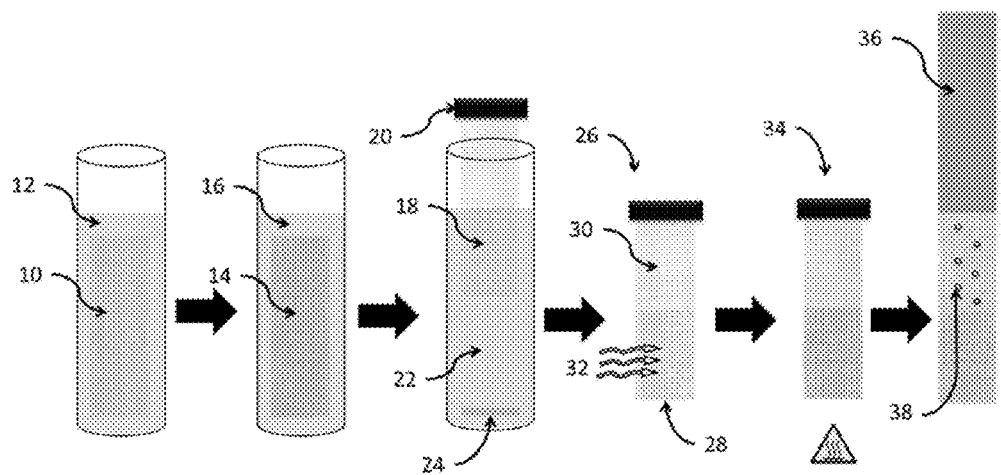
FIG. 1 is an illustration that shows the overall procedure for the preparation of the SPME-TM devices including two main steps: preparation of the coating as well as welding of the coated mesh on the solid substrate.

The transitional term "comprising" is synonymous with "including" or "containing" and is inclusive or open-ended and does not exclude additional, unrecited elements or method steps.

The transitional phrase "consisting of" excludes any feature, element, step, or ingredient not specified in the claim, but does not exclude additional components or steps that are unrelated to the invention such as impurities ordinarily associated with a composition.

The transitional phrase "consisting essentially of" limits the scope of a claim to the specified materials, features or steps and those that do not materially affect the basic and novel characteristic(s) of the claimed invention.

The subject matter disclosed herein relates to systems and methods that extract or enrich analytes of interest present in a sample, and that are then coupled to a thermal or solvent based desorption source of a mass spectrometer. The thermal or solvent based desorption source may use a heated gas with electronic excited-state species to desorb a molecule sorbed on the surface of the extractive device. The desorption source may be a direct analysis in real-time (DART) source.

The system disclosed herein, when the extractive phase includes a polymer and solid phase microextraction (SPME) particles, may be referred to as solid phase microextraction-transmission mode (SPME-TM) as it can be used without further modification as a transmission mode (TM) substrate for desorbing a molecule that is adsorbed on the surface of the SPME device using a thermal or solvent based desorption technique. SPME-TM may integrate sample preparation and ambient ionization.

The thermal or solvent based desorption device may use a heated gas with electronic excited-state species to desorb analytes that are sorbed on the extractive device. The heated gas with electronic excited-state species may be generated through, for example: Plasma Assisted Desorption/Ionization (PADI), Dielectric Barrier Discharge ionization (DBDI or DCBI), Desorption Atmospheric Pressure Chemical Ionization (DAPCI), Desorption Sonic Spray Ionization (DeSSI), Desorption Atmospheric Pressure Photoionization (DAPPI), Flowing Atmospheric-Pressure Afterglow (FAPA), desorption electrospray ionization (DESI), atmospheric laser desorption ionization, corona discharge, inductively coupled plasma (ICP), or glow discharge.

A solid-phase microextraction transmission mode (SPME-TM) device includes a mesh substrate that is coated with an extractive coating that includes a polymer, preferably a biocompatible polymer, and solid phase microextraction (SPME) particles having pores dimensioned to adsorb a molecule of interest from a matrix. The polymer covers the SPME particles, but still allows at least some of the analytes of interest present in the matrix to be adsorbed by the SPME particles. Non-biocompatible polymer can be used to bind the particles when non-biological samples are analyzed. An alternative device according to the present disclosure includes a mesh substrate that is coated with an extractive coating that includes a polymer that absorbs a molecule of interest from a matrix.

In one exemplary method of extracting a compound of interest from a sample matrix and detecting the extracted compound, a coating on a coated mesh substrate is placed in a methanol:water solution (50:50) at least 15 minutes before extraction in order to improve the interaction between the coating surface and the analytes present in the matrix. Although this exemplary method discusses a conditioning step using a methanol:water solution, it should be understood that this conditioning step may result in better extraction with only some coatings, such as coatings that include C-18 particles, and may not improve extraction with coatings that include other particles, such as HLB particles.

The conditioned coated mesh substrate is subsequently inserted in a sample matrix and extraction or enrichment of the analyte is performed by agitating the sample at high speed (e.g. vortex agitation at 3200 rpm, t≤1 min). The coated mesh substrate is subsequently rinsed in a vessel containing LC/MS grade water (t≤10 s) to remove potential at least some artefacts adhered to the coating surface. In this exemplary method, the coated mesh substrate is subsequently installed on a mesh-holder (which allows the easy and fast replacement of the SPME-TM devices), which is positioned in an automatic linear rail that places the SPME-TM device in front of the DART nozzle. As discussed above, methods according to the present disclosure may place the coated mesh substrate in front of a nozzle for a different ionization device.

Sensitivity by SPME-TM can be enhanced towards an specific compound by changing: the characteristics of the mesh substrate (i.e. mesh material type, empty space diameter, consecutive hole to hole distance, and strand size); the characteristics of the coating (i.e. polymeric phase chemistry, particle size, porosity, thermal conductivity, thermal stability, and affinity for the analyte of interest); the operating parameters of the desorption device, such as gas temperature and flow, discharge voltage, grid electrode voltage, or spatial position of the mesh in relation to the ion source nozzle, in order to balance between efficient neutral generation by thermal desorption and transport into the mass spectrometer.

Coated mesh substrates can be used for in vitro analysis of drug concentrations as well as for in situ analysis of contaminants, such as in a river stream. Coated mesh for in vitro analysis of biofluids can have any combination of extractive particles coated with an appropriate biocompatible coating, such as polyacrylonitrile (PAN), polyethylene glycol, polypyrrole, derivatised cellulose, polysulfone, or polyamide solution. Non-limiting examples of the coating include: a PAN/C-18 coating, a PAN/HLB coating, a PAN/RP-amide coating, a polyethylene glycol/HS-F5 coating, a derivatised cellulose/C-18 coating, a polypyrrole/C-30 coating, a polysulfone/phenyl coating and polyamide/cyano coating.

A coated mesh substrate may be produced using a batch-coating process. In an exemplary batch-coating process, the coating was applied on the mesh by dipping the mesh into a vessel containing a suspension of extraction particles in a biocompatible coating solution. The desired coating area of the mesh was immersed in this solution for 15 seconds and then removed at a speed of about 0.1 to about 0.5 mm per second. Then, a flow of nitrogen of 1.5 L/min was used to remove the excess of coating slurry accumulated on the openings of the mesh. After applying one layer of coating, the coated blade was passed through a heater at an elevated temperature. In the exemplary batch-coating process, the steps noted above were repeated five times until the desired thickness was obtained. The rate of removal of the mesh substrate from the suspension of extraction particles can affect the interaction between the slurry and the mesh substrate. A removal rate of about 0.1 to about 0.5 mm/second results in desirable interactions between the slurry and the mesh substrate.

In a batch-coating process, multiple thin layers of the suspension can be applied to the mesh substrate until the desired coating thickness is obtained. The advantage of applying multiple layers is that each coating layer is bonded and the coating thickness is uniform throughout the desired length on the mesh substrate. When the process parameters are controlled by automation, reproducibility between meshes can be greatly improved.

The meshes can be pre-processed before the coating process in order to clean and roughen the surface. Pre-processing can be accomplished by washing with acetone, etching for 5 min in concentrated hydrochloric acid, washing the mesh with water and/or thoroughly cleaning the mesh by sonication in methanol. Prior to use, the coated mesh can be conditioned in water:methanol 50:50 wash for 30 min. Conditioning the C-18 based coatings with water or higher proportion of methanol can lead to worse reproducibility. Other coatings, however, can require only a very brief conditioning step (less than 5 min), or even none at all.

In one example of a device according to the present disclosure, discussed in greater detail below, the coated mesh substrate (2.5×0.4 cm, where the coating is 1×0.4 cm, L×W) is welded on a sheet (4.2×0.4 cm, L×W) that can be constructed of any material. Preferably, the substrate used to construct the sheet is stainless steel or nitinol. A sheet of the size noted above allows the sheet to be used as a handle for manipulating the coated mesh substrate. Manipulating the handle, and not the coated mesh substrate, reduces the possibility that the coated mesh substrate is contaminated, and minimizes or prevents the contact of the analyst with the sample.

One example of a batch-coating process is illustrated in FIG. 1. A non-coated mesh (10) is etched in a solution (12) of hydrochloric acid (37% by volume). The etched mesh (14) is cleaned in methanol (16). The cleaned mesh (18) is held with a temporary handle (20) and is dipped in a coating solution (22) that is stirred using a stir bar (24) to ensure the coating solution is well mixed. The coated mesh substrate (26) has a coated area (28) and a non-coated area (30). Excess coating solution is removed from the coated area (28) by flowing nitrogen (32) through the mesh. The coated mesh substrate having excess coating removed (34) is heated at 125° C. to remove solvent. The coating, nitrogen, and heating steps are repeated as desired. The dried coated mesh substrate (34) is removed from the temporary handle (20) and is attached to a support handle (36), for example through welding points (38).

Experiment 1

Preparation of Exemplary Devices

Figure 2:
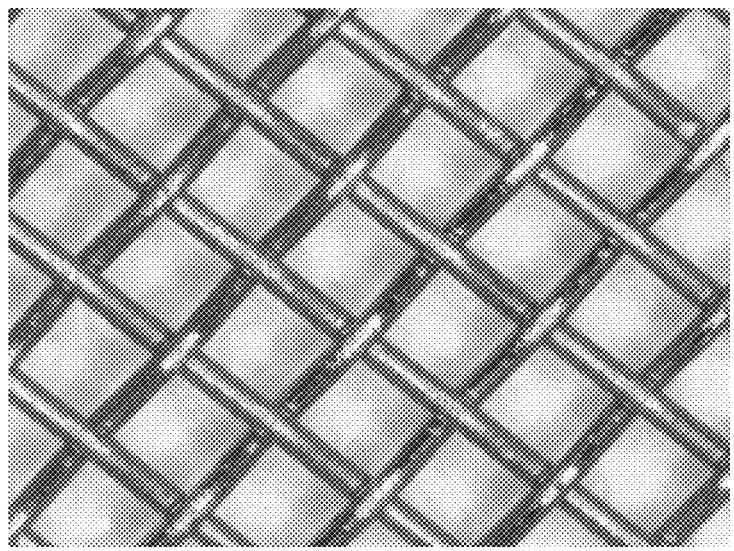
FIG. 2 is a photograph that shows a bare stainless steel mesh (74×74 wires in$^{-1}$) after etching and conditioning.

A SPME-TM device was prepared as follows: a stainless steel mesh (74×74 wires/in, wire diameter 0.004 in) with a length of 2.5 cm and width of 0.4 cm was etched for 5 min in concentrated hydrochloric acid (37% vol/vol), washed with water, and cleaned by sonication in methanol. A photograph of the etched mesh is shown in FIG. 2. The etched mesh was stored in an inert atmosphere in a desiccator in order to prevent oxidation or significant changes of surface prior to coating.

A coating solution, 0.18 wt/wt PAN/C18 particles ratio and 1% wt/wt PAN/DMF ratio, was prepared. The coating solution was continuously agitated at a speed of 1000 rpm using an octagonal stir bar (12×4.5 mm). Coatings were applied on the strands of the mesh substrate by dipping the mesh for 15 seconds into a small vessel containing the coating solution, and the mesh was removed at a speed ranging between 0.1 to 0.5 mm/s. The actual coated area has a length of 1 cm and width of 0.4 cm. Subsequently, nitrogen was flowed through the coated mesh substrate ($\leq$1.5 L min$^{-1}$) to dry the coating on the wires and to remove excess slurry trapped on the mesh openings. The coating was cured for about 1.5 min at 125° C.

Figure 3:
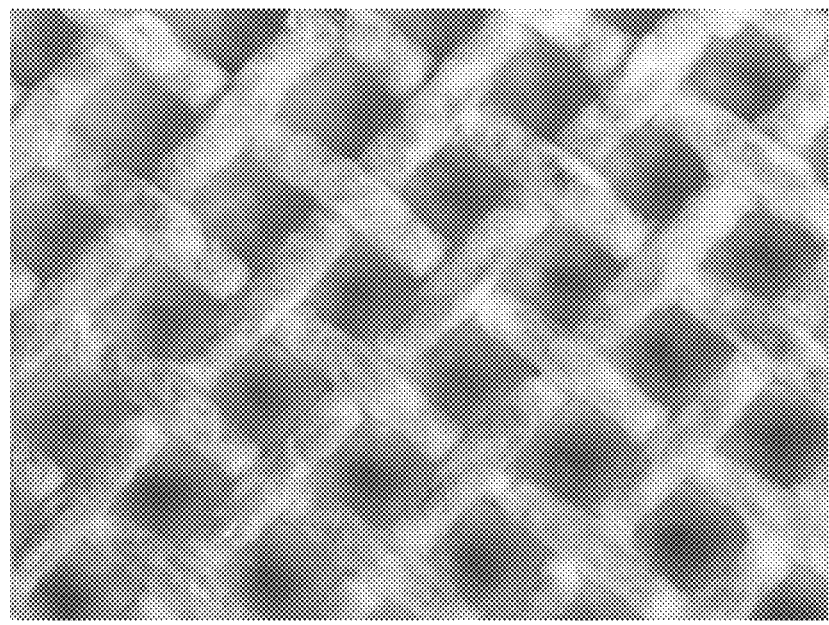
FIG. 3 is a photograph that shows a stainless steel mesh coated with C18-PAN after 5 coating steps.
Figure 4:
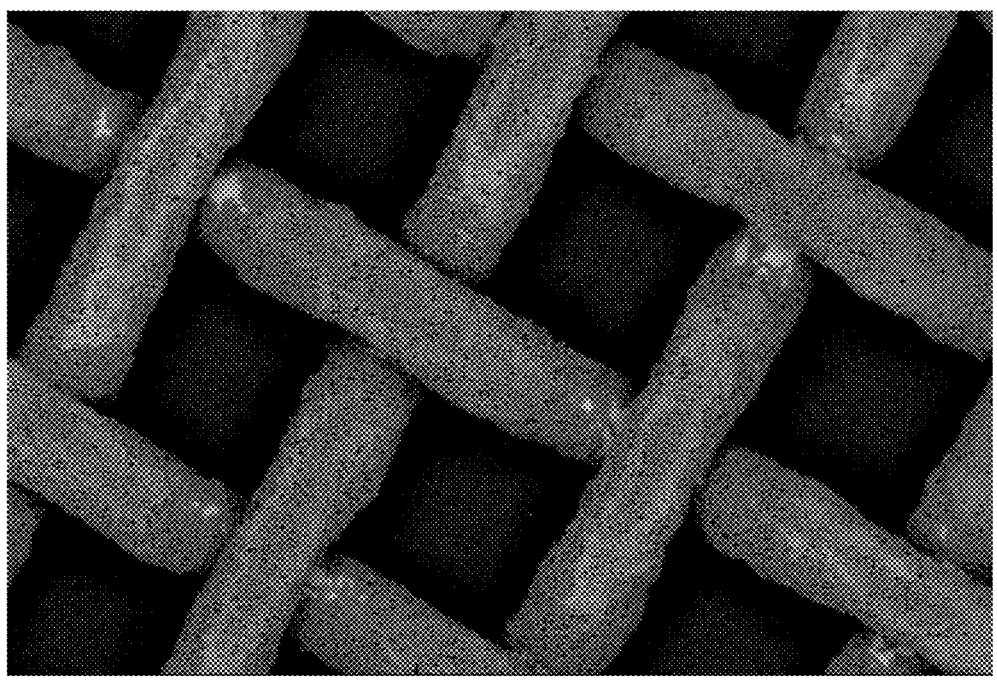
FIG. 4 is an SEM image of a stainless steel mesh coated with C18-PAN after 5 coating steps.
Figure 5:
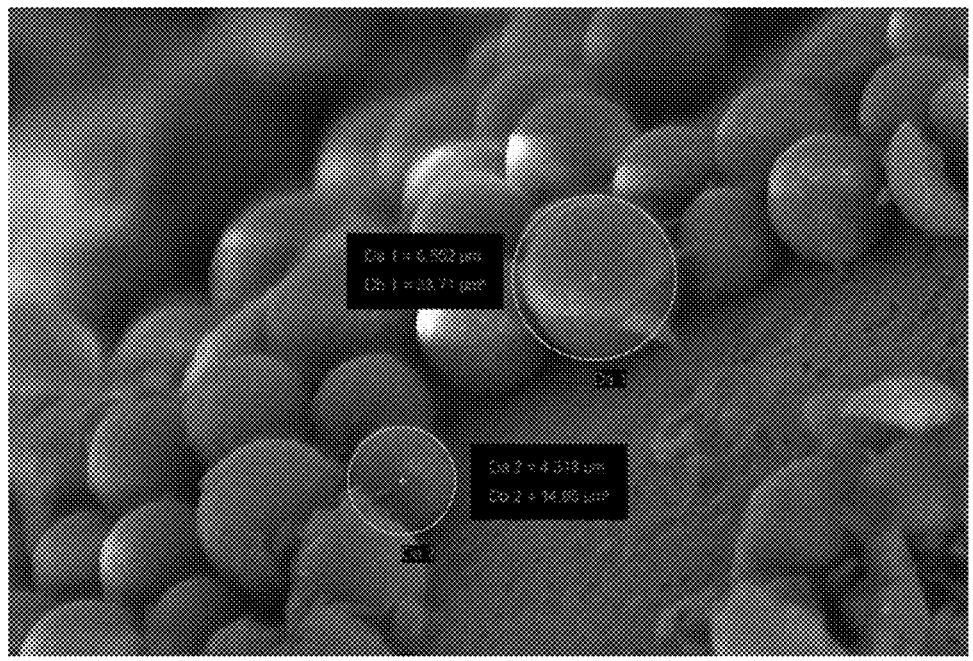
FIG. 5 is an SEM image of the particle size C18 attached to the surface of the mesh after 5 coating steps.
Figure 6:
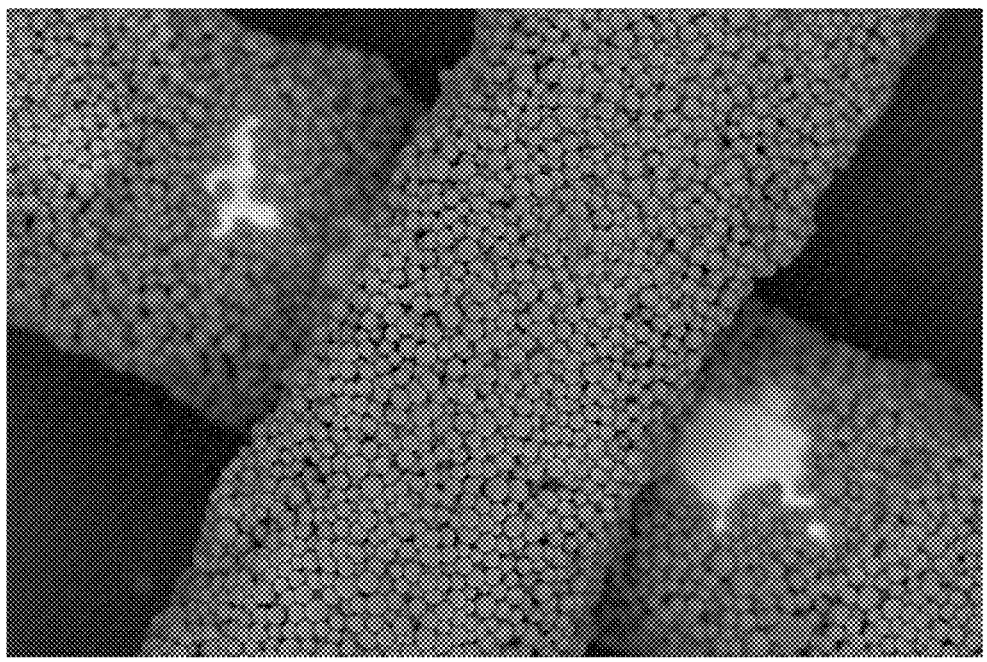
FIG. 6 is an SEM image of two filaments/strings coated with C18-PAN after 5 coating steps.

The coating process was repeated until the desired thickness was obtained. It was found that 5 or fewer cycles was enough to obtain a thin layer of coating. A photograph of the coated mesh substrate is shown in FIG. 3, and scanning electron micrographs of the coated mesh substrate are shown in FIG. 4-6.

Figure 7:
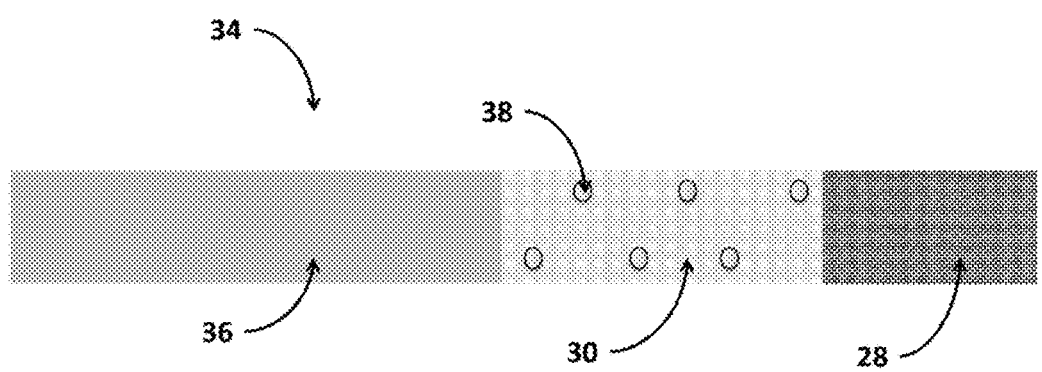
FIG. 7 is an illustration that shows a scheme of the design used to construct the mesh-blade configuration used for the SPME-TM devices.

The coated mesh substrate (34) has a coated area (28) and a non-coated area (30). The non-coated area (30) was arc welded to a support handle (36) made of a stainless steel sheet that is 4.2×0.4 cm (L×W). In order to provide a strong attachment between the mesh and the solid substrate, the mesh was welded on 6 points (as illustrated in FIG. 7). The stainless steel sheet could alternatively be fabricated of any biocompatible material, e.g. nitinol. The coated mesh could alternatively be attached or glued to other biocompatible and chemically inert material, such as Teflon or polybutylene terephthalate or a 3D printing material.

Experiment 2

Analytical Process for Exemplary Devices

Figure 8:
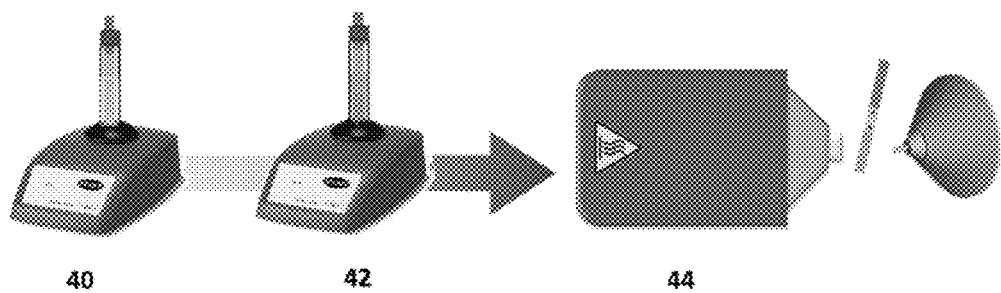
FIG. 8 is an illustration that shows the experimental set up for SPME-TM extraction and desorption/ionization using direct analysis in real time (DART).

An exemplary analytical process with SPME-TM, is illustrated in FIG. 8. As illustrated in step (40), a coated mesh substrate prepared according to Experiment 1 was inserted in a vial containing a sample matrix (300-1500 μL) and extraction and enrichment was performed by agitating at the sample at high speed (vortex agitation at 3200 rpm, t≤1 min). The coated mesh substrate was rinsed at (42) in a vial containing water (1500 μL, t≤10 s) to remove at least some artefacts adhered to the coating surface. The coated mesh substrate was installed on a holder, which allows the easy and fast replacement of the coated mesh substrate. Then holder is positioned in an automatic linear rail that moves the mesh between the DART nozzle and the MS inlet (with all three coaxial to one-another, 0° angle). As illustrated in step (44), a metastable gas stream was flowed through the mesh performing simultaneous desorption and ionization of the compounds sorbed on the surface of the coating particles. Ions of the extracted or pre-concentrated analytes were transported into the atmospheric pressure interface (API) and analyzed by tandem mass spectrometry.

Figure 9:
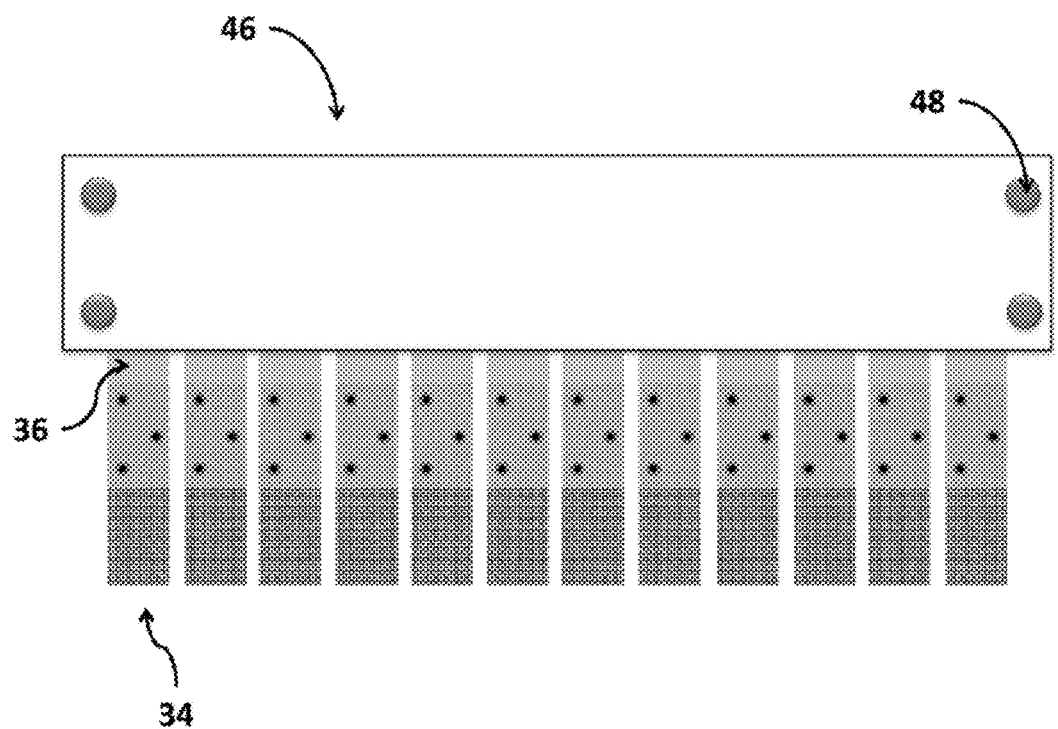
FIG. 9 is an illustration that shows a scheme of the holder for SPME-TM for automated and stable desorption/ionizations using DART.

FIG. 9 illustrates a holder (46) that holds 12 coated mesh substrates (34) by the support handles (36). The holder (46) holds the coated solid substrates (34) in a configuration that allows them to be inserted into one row of a 96-well plate. The holders (46) include magnets (48) that are positioned to attach one holder to an adjacent holder. The holder (46) is sized and shaped so that 8 holders attached together allow the coated solid substrates to be inserted into the 8 rows of a 96-well plate. The 8 attached holders, each holding 12 coated solid substrates, allow each of the 96 coated solid substrates to be inserted into each of the 96 wells.

Figure 10:
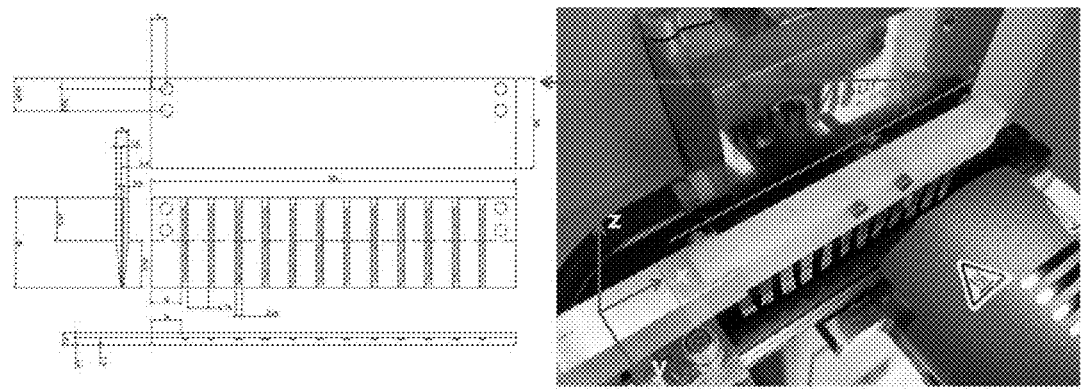
FIG. 10 is a schematic of 12-SPME-TM DART holder. It can be used not only to perform concomitant extractions on a 96 well autosampler, but also automated and stable desorption/ionizations. The system is compatible with the automated rail commercialized by IonSense. Up to 12 SPME- TM devices can be easily installed or removed from the holder and spatial position can be accurately adjusted on the Z and Y axis.

FIG. 10 shows and illustrates an automatic linear rail that sequentially moves each coated mesh substrate between the DART nozzle and the MS inlet.

Experiment 3

Detection Capabilities of Exemplary Devices

It has been incorrectly assumed by scientist not familiar with SPME that extraction and enrichment cannot be performed in short periods of time. In the context of the present disclosure, a short extraction time would be understood to mean extraction times of 60 seconds or less. High surface area contact between extraction phase and the matrix facilitates high mass transfer rates. The thin coatings ensure rapid equilibration times and efficient desorption to MS instrument. Additionally, it is also assumed by scientist not familiar with SPME that extractions should be performed at equilibrium to achieve lower LOD/LOQ.

Figure 11:
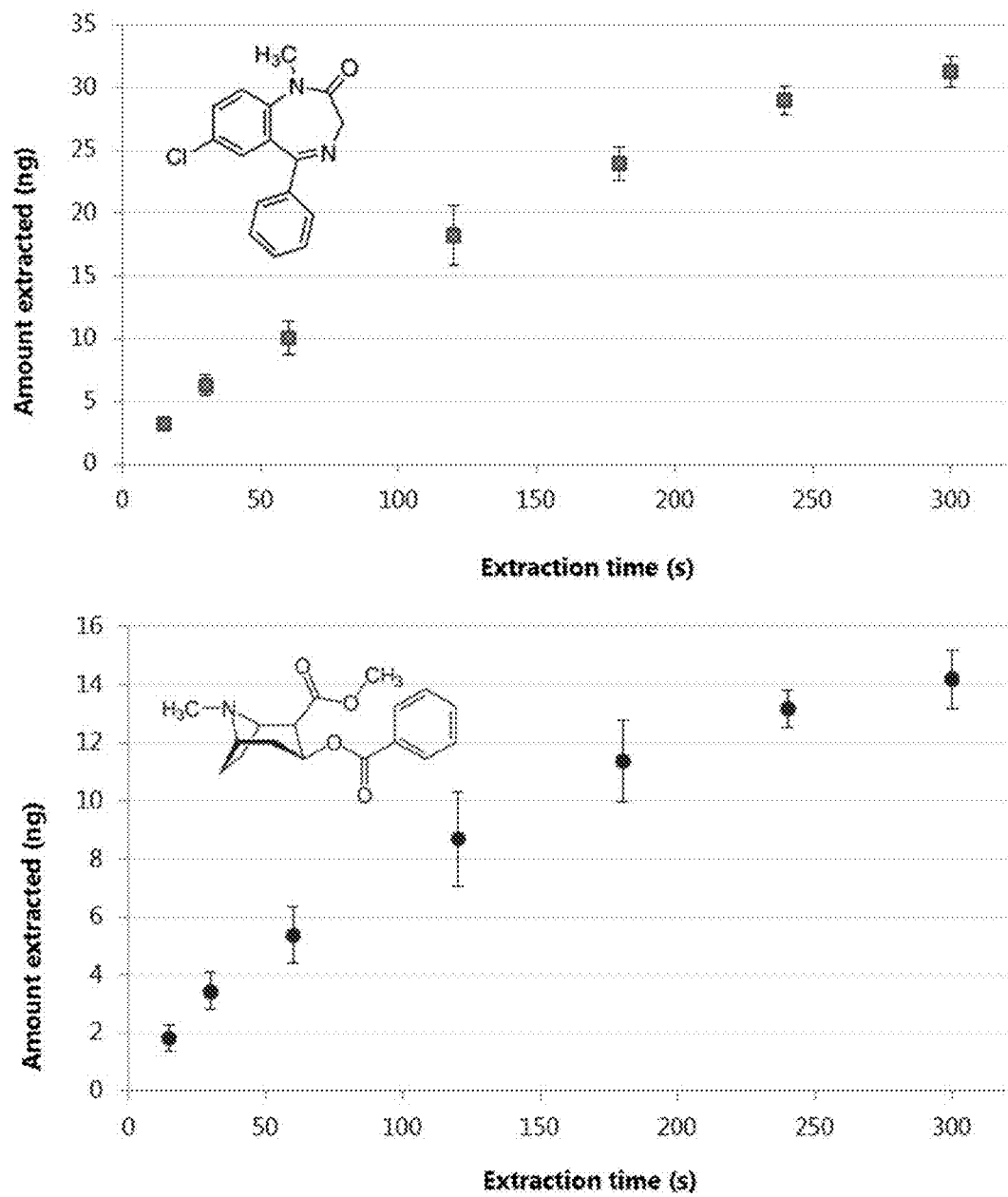
FIG. 11 is a graph that shows extraction time profiles for diazepam and cocaine, respectively. Extractions were performed using vortex agitator set-up at maximum speed (3200 rpm). Extractions from 1.5 mL of PBS spiked with 50 ppb of each analyte with 3 different TFME devices (n=6) for each extraction point. Extracts were analyzed using Thermo LC/MS on SRM mode.
Figure 12:
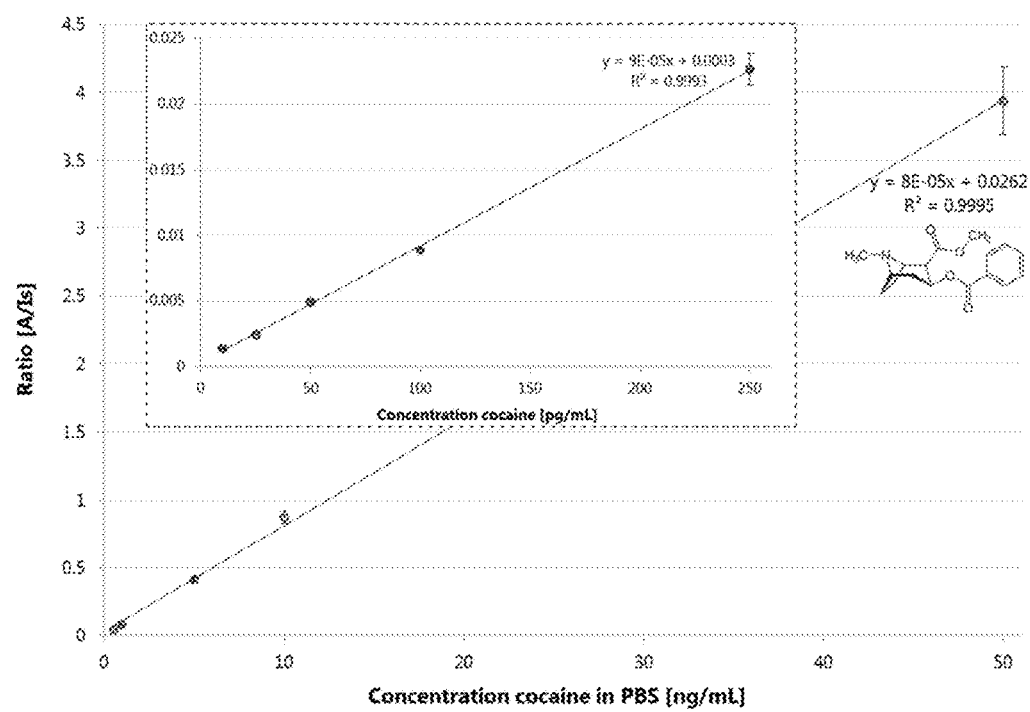
FIG. 12 is a graph that shows quantitative analysis of PBS spiked with cocaine (10 pg mL$^{-1}$ to 50 ng mL$^{-1}$) and its isotopologue [D$_3$] cocaine (12 ng mL$^{-1}$). Bars represent the standard deviation of analysis for three replicates with independent SPME-TM devices.
Figure 13:
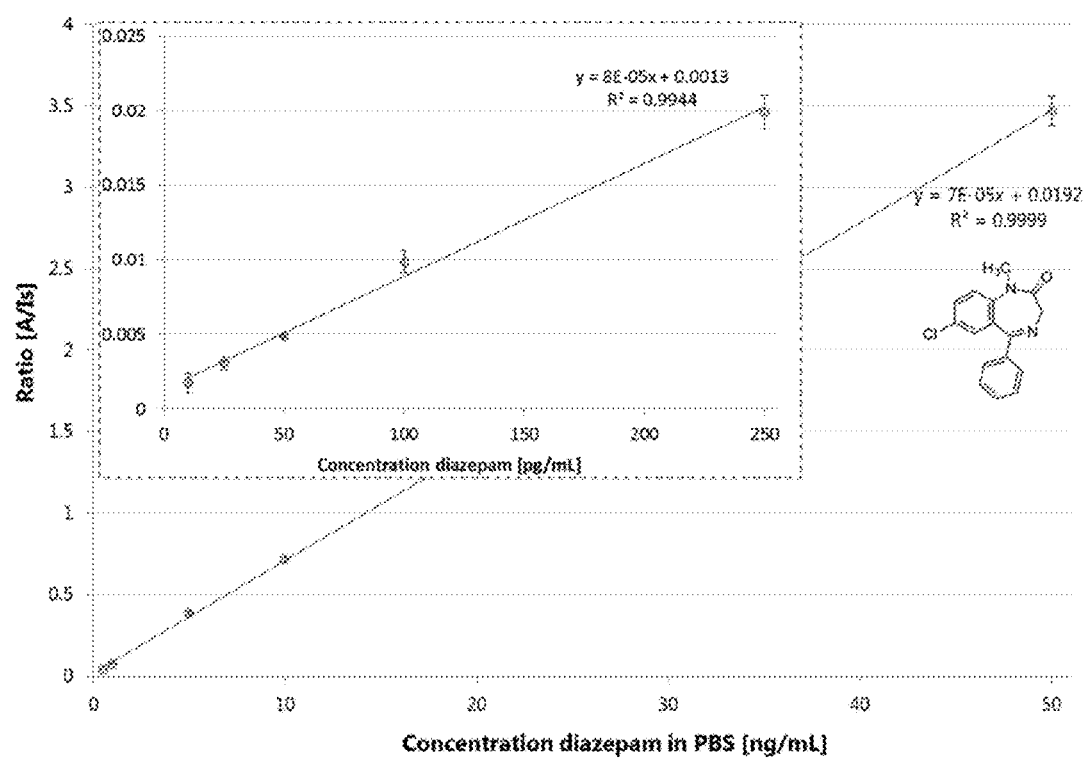
FIG. 13 is a graph that shows quantitative analysis of PBS spiked with diazepam (10 pg mL$^{-1}$ to 50 ng mL$^{-1}$) and its isotopologue [D$_5$] diazepam (12 ng mL$^{-1}$). Bars represent the standard deviation of analysis for three replicates with independent SPME-TM devices.

Given that the dilution factor inherent in most SPME-LC methods is removed from the analytical procedure, methods and devices disclosed herein outperform traditional detection limits with remarkably brief extraction times. Hence, the LOD associated with methods and devices disclosed herein is mainly constrained by the detection capabilities of the MS system rather than by built-in features of the coating. Experiments using thin-film microextraction devices (TFME, blade geometry as illustrated in FIG. 7) showed that 15 seconds is sufficient to extract a quantifiable amount of analyte at the low ppb level even when using the traditional LC/MS approach. Results of these experiments are shown in FIG. 11. Indeed, if lower LOD are required, the interaction time between the coating and the sample matrix can be increased. For instance, LOQ as low as 2 and 19 pg mL$^{-1}$ were reached when performing 1 minute extraction from 1.5 mL of phosphate buffered saline (PBS) spiked with cocaine and diazepam (DZP), respectively. Furthermore, the linear dynamic range of the method, evaluated from 10 pg mL$^{-1}$ up to 50 ng mL$^{-1}$, showed astounding linearity. Results of these experiments are shown in FIGS. 12 and 13. It is worth emphasizing that higher concentration levels are not a limitation for SPME. Indeed, if there is the case in which a compound is present at high concentration (i.e. ppm levels) and the affinity of the coating for the analyte is strong, shorter extraction times (e.g. ≤30 s) can be performed.

Experiment 4

Intra- and Inter-Device Reproducibility of Exemplary Devices

Figure 14A:
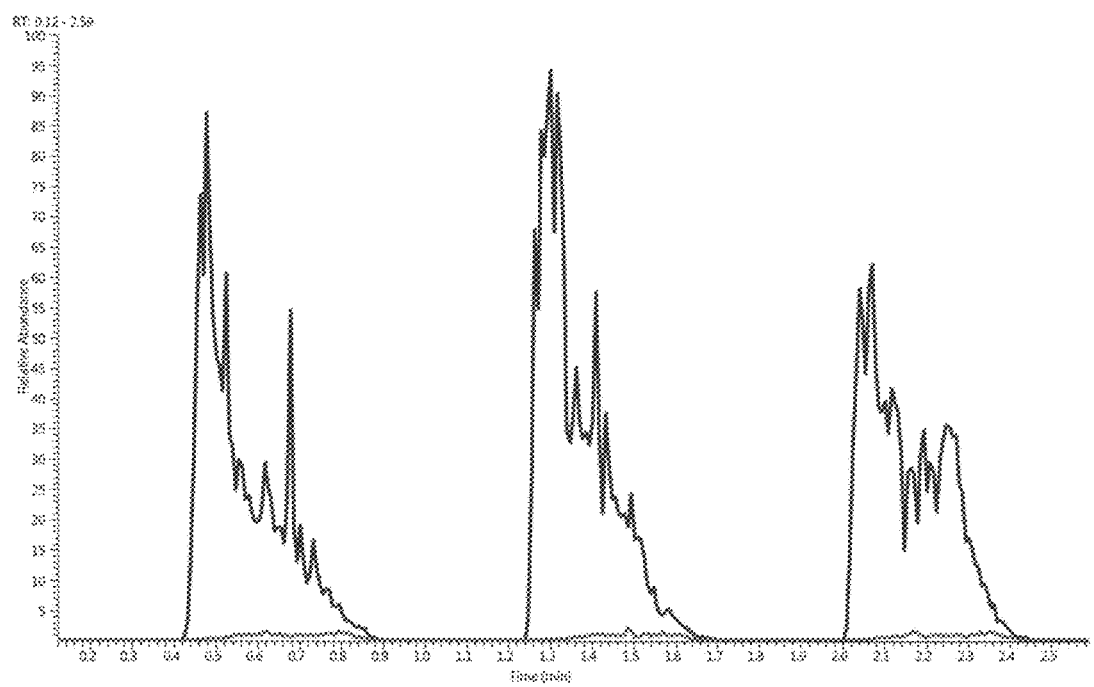
FIGS. 14A and 14B are graphs that show SPME-TM inter-mesh reproducibility; ion chronograms obtained after 1 min extraction from a solution spiked with 20 ppb of cocaine versus carry-over after 1 desorption/ionization cycle (FIG. 14A) or carry-over after 1 cleaning step (FIG. 14B).
Figure 14B:
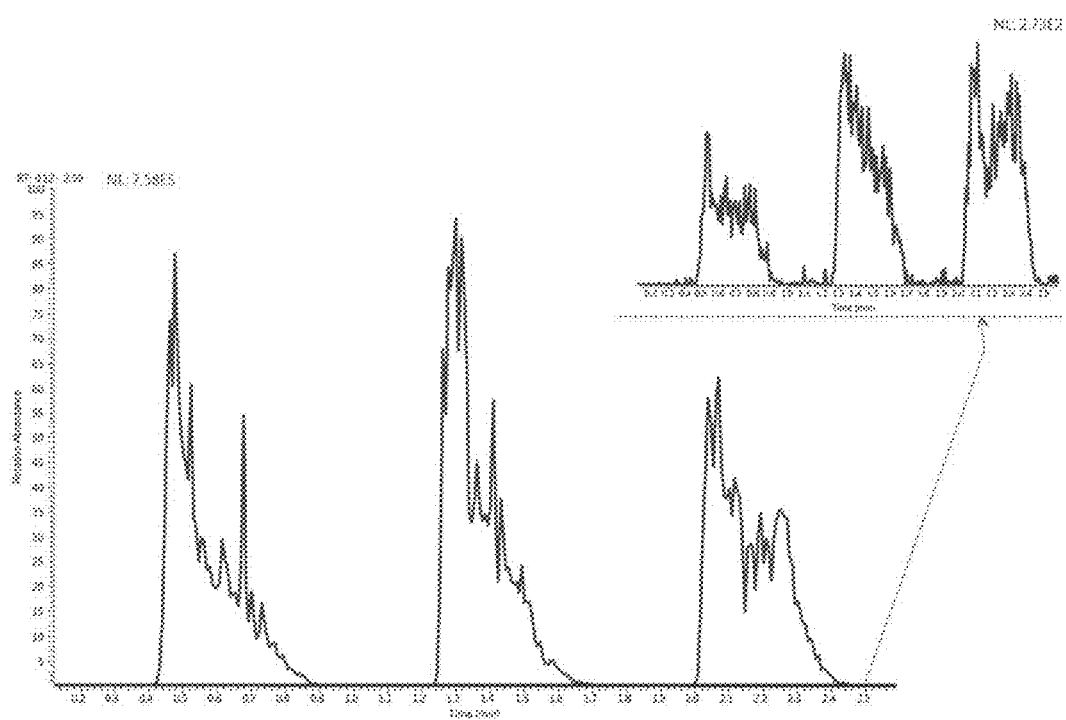
Figure 15:
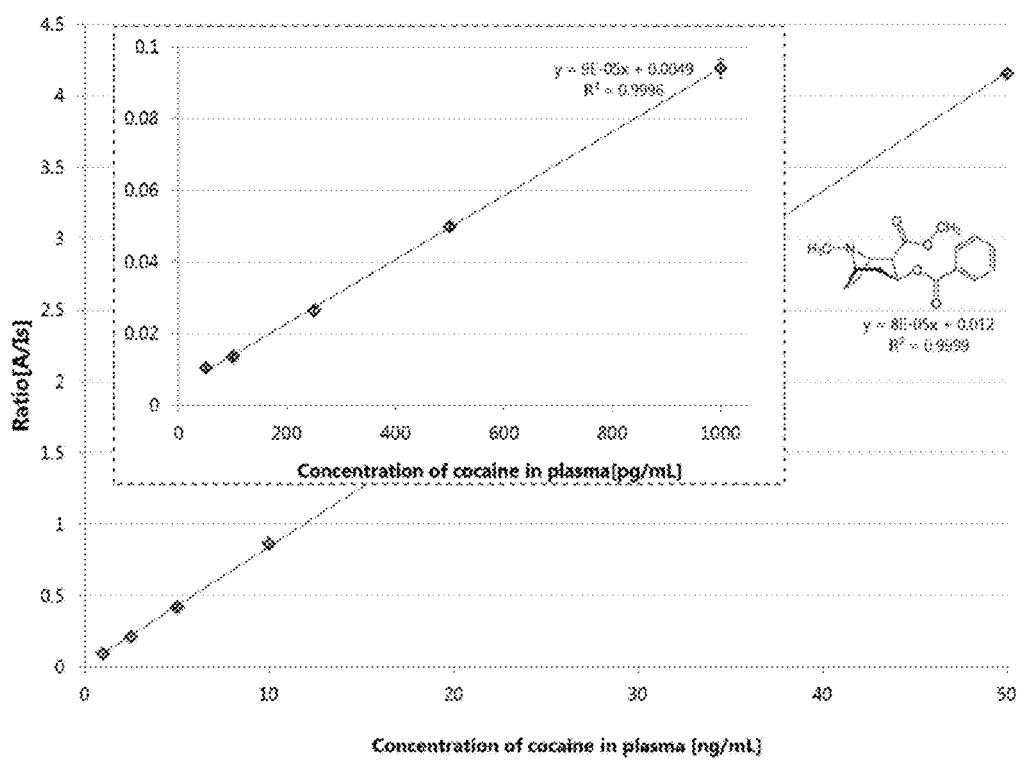
FIG. 15 is a graph that shows quantitative analysis of plasma spiked with cocaine (50 pg mL$^{-1}$ to 50 ng mL$^{-1}$) and its isotopologue [D$_3$] cocaine (12 ng mL$^{-1}$).
Figure 16:
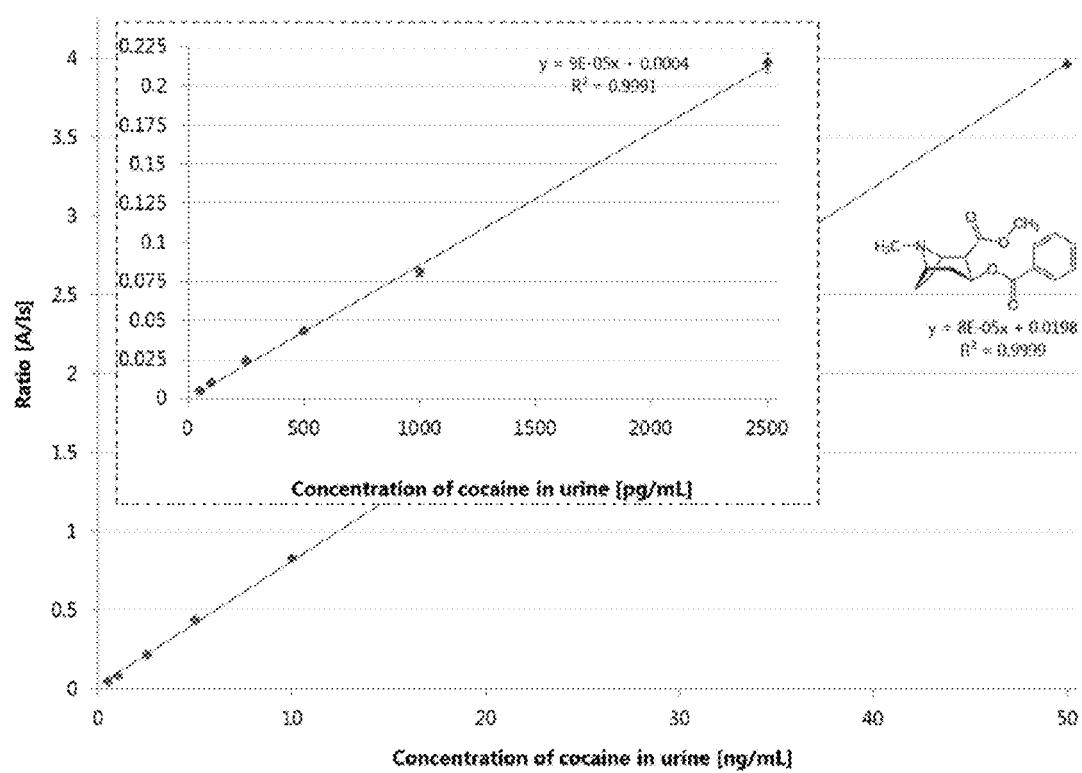
FIG. 16 is a graph that shows quantitative analysis of urine spiked with cocaine (50 pg mL$^{-1}$ to 50 ng mL$^{-1}$) and its isotopologue [D$_3$] cocaine (12 ng mL$^{-1}$).
Figure 17:
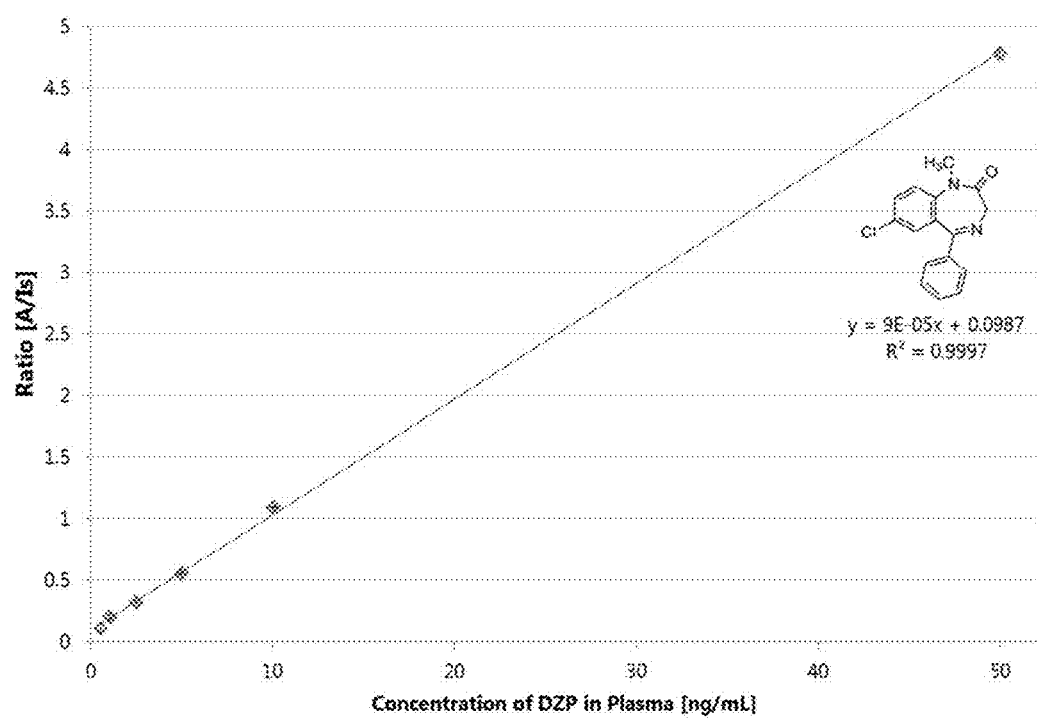
FIG. 17 is a graph that shows quantitative analysis of plasma spiked with diazepam (500 pg mL$^{-1}$ to 50 ng mL$^{-1}$) and its isotopologue [D$_5$] diazepam (12 ng mL$^{-1}$).
Figure 18:
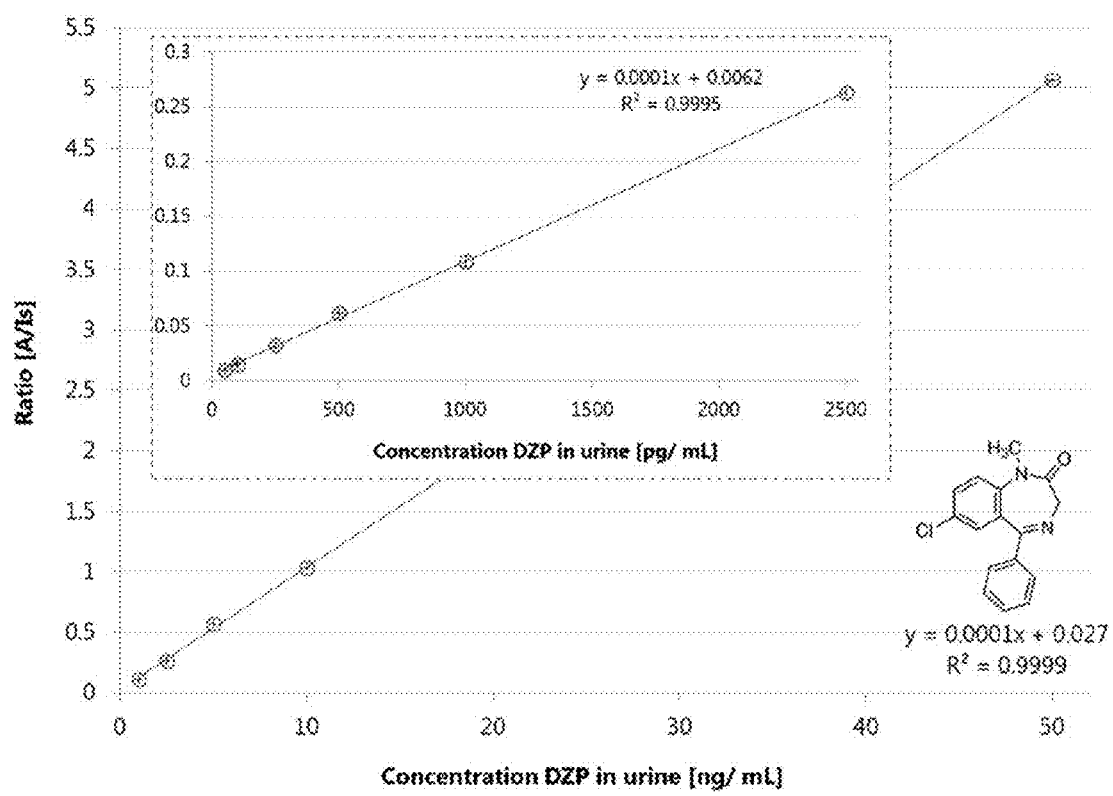
FIG. 18 is a graph that shows quantitative analysis of urine spiked with diazepam (50 pg mL$^{-1}$ to 50 ng mL$^{-1}$) and its isotopologue [D$_5$] diazepam (12 ng mL$^{-1}$).

A unique feature of the devices disclosed in Experiment 1 in comparison with other ambient mass spectrometry devices is their reusability. Extractions performed with 9 independent devices (n=36) from 1.5 mL of PBS solution spiked with cocaine and diazepam showed intra-/inter-device reproducibility lower than 4.7 and 3.2%, respectively (Table 1-5). Certainly, herein is confirmed that by using thin-coatings not only efficient mass transfer of the analytes is achieved (fast extractions), but also effective desorption. In addition, despite that it was found that the signal obtained on a second desorption and ionization cycle (carryover) was approximately 5% of signal use for quantitation of DZP (FIG. 14A), it is important to highlight that detection of DZP and cocaine was performed concomitantly. Thus, DART experimental conditions were not exclusively optimized for DZP and this could explain why a small fraction of analyte still remained after the first desorption and ionization cycle. Nevertheless, by implementing a cleaning step shortly after the desorption and ionization cycle (i.e. mixture of methanol, isopropanol and acetonitrile; 50:25:25) negligible carryover was attained (≤0.4%, FIG. 14B). The cleaning step could be optimized according to both the chemistry of the coating and its affinity towards the analyte of interest. In cases where there is an extensive variation in analyte concentration among samples (i.e. low ppt to ppm levels) devices could preferably be restricted to a single use. Otherwise, a few amount of analyte could remain on the coating, even after the cleaning cycle, and cause potential false positives. While working with compounds at concentrations greater than 50 ppb and with high affinity towards the coating, shorter extractions can be performed (≤30 s). Extracting with shorter extraction times reduces the amount of analyte enriched and the complete removal of the analytes that are not desorbed by DART, or other solvent or thermally based ionization approaches, is possible when including the cleaning step.

TABLE 1

SPME-TM inter-device reproducibility.

| Experiment | Ratio [A/Is] | SD | RSD [%] | % Carryover DART [$A_c/A_i$] | % Carryover solvent [$A_c/A_i$] |
|---|---|---|---|---|---|
| Diazepam | 1.8 | 0.05 | 3 | 5 | 0.3 |
| Cocaine | 1.6 | 0.05 | 3 | 2.4 | 0.2 |

SD, standard deviation; RSD, relative standard deviation.

Ratio [Analyte/Isotopologue] results correspond to the average of extractions performed with 9 independent devices (n = 36) from a PBS solution spiked with 20 ppb of each analyte.

TABLE 2

Inter- and intra-mesh reproducibility (n = 36). Results are reported as ratio of analyte (diazepam) versus internal standard isotopologue [$D_5$] diazepam. 1 min extractions were performed using vortex agitator set-up at maximum speed (3200 rpm). Extraction from 1.5 mL of PBS spiked with 20 ng mL$^{-1}$ of each substance. Analyses were performed using Thermo TSQ on SRM mode.

| Experiment | Mesh_1 | Mesh_2 | Mesh_3 | Mesh_4 | Mesh_5 | Mesh_6 | Mesh_7 | Mesh_8 | Mesh_9 |
|---|---|---|---|---|---|---|---|---|---|
| Replicate 1 | 1.9 | 1.8 | 1.9 | 1.8 | 1.8 | 1.7 | 1.8 | 1.8 | 1.8 |
| Replicate 2 | 1.9 | 1.8 | 1.8 | 1.8 | 1.8 | 1.8 | 1.7 | 1.8 | 1.7 |
| Replicate 3 | 1.8 | 1.8 | 1.8 | 1.8 | 1.8 | 1.8 | 1.8 | 1.8 | 1.8 |
| Replicate 4 | 1.8 | 1.8 | 1.9 | 1.9 | 1.8 | 1.8 | 1.8 | 1.7 | 1.8 |
| Average | 1.8 | 1.8 | 1.8 | 1.8 | 1.8 | 1.8 | 1.8 | 1.8 | 1.8 |
| SD | 0.07 | 0.02 | 0.09 | 0.04 | 0.02 | 0.04 | 0.01 | 0.03 | 0.03 |
| RSD | 3.6 | 1.2 | 4.6 | 2.1 | 1.4 | 2.0 | 0.7 | 1.9 | 1.9 |

SD, standard deviation.
RSD, relative standard deviation.

TABLE 3

Inter- and intra-mesh reproducibility (n = 36). Results are reported as ratio of analyte (cocaine) versus internal standard isotopologue [$D_3$] cocaine 1 min extractions were performed using vortex agitator set-up at maximum speed (3200 rpm). Extraction from 1.5 mL of PBS spiked with 20 ng mL$^{-1}$ of each substance. Analyses were performed using Thermo TSQ on SRM mode.

| Experiment | Mesh_1 | Mesh_2 | Mesh_3 | Mesh 4 | Mesh_5 | Mesh_6 | Mesh_7 | Mesh_8 | Mesh_9 |
|---|---|---|---|---|---|---|---|---|---|
| Replicate 1 | 1.5 | 1.5 | 1.5 | 1.6 | 1.5 | 1.6 | 1.6 | 1.6 | 1.6 |
| Replicate 2 | 1.5 | 1.5 | 1.6 | 1.6 | 1.6 | 1.6 | 1.6 | 1.6 | 1.6 |
| Replicate 3 | 1.5 | 1.5 | 1.6 | 1.5 | 1.6 | 1.6 | 1.7 | 1.6 | 1.5 |
| Replicate 4 | 1.5 | 1.5 | 1.5 | 1.5 | 1.5 | 1.5 | 1.6 | 1.6 | 1.5 |
| Average | 1.5 | 1.5 | 1.5 | 1.6 | 1.5 | 1.6 | 1.6 | 1.6 | 1.6 |
| SD | 0.03 | 0.02 | 0.05 | 0.04 | 0.07 | 0.03 | 0.04 | 0.04 | 0.05 |
| RSD | 2.1 | 1.0 | 3.3 | 2.8 | 4.7 | 1.7 | 2.2 | 2.8 | 3.3 |

SD, standard deviation.
RSD, relative standard deviation.

TABLE 4

Inter- and intra-mesh carry-over (n = 36). Results are reported as ratio of analyte (diazepam) versus internal standard isotopologue [$D_5$] diazepam. 1 min extractions were performed using vortex agitator set-up at maximum speed (3200 rpm). Extraction from 1.5 mL of PBS spiked with 20 ng mL$^{-1}$ of each substance. Analyses were performed using Thermo TSQ on SRM mode.

| Experiment | [A/Is] | SD | RSD | % Carryover DART [A2/A1] | % Carryover solvent [A2/A1] |
|---|---|---|---|---|---|
| Replicate 1 | 1.8 | 0.06 | 3.2 | 7.2 | 0.5 |
| Replicate 2 | 1.8 | 0.04 | 2.4 | 4.4 | 0.3 |
| Replicate 3 | 1.8 | 0.03 | 1.9 | 4.3 | 0.3 |
| Replicate 4 | 1.8 | 0.06 | 3.1 | 3.9 | 0.2 |
| Average | 1.8 | 0.05 | 2.7 | 5.0 | 0.3 |

SD, standard deviation.
RSD, relative standard deviation.

TABLE 5

Inter- and intra-mesh carry-over (n = 36). Results are reported as ratio of analyte (cocaine) versus internal standard isotopologue [$D_3$] cocaine. 1 min extractions were performed using vortex agitator set-up at maximum speed (3200 rpm). Extraction from 1.5 mL of PBS spiked with 20 ng mL$^{-1}$ of each substance. Analyses were performed using Thermo TSQ on SRM mode.

| Experiment | [A/Is] | SD | RSD | % Carryover DART [A2/A1] | % Carryover solvent [A2/A1] |
|---|---|---|---|---|---|
| Replicate 1 | 1.6 | 0.05 | 3.4 | 3.1 | 0.5 |
| Replicate 2 | 1.6 | 0.03 | 2.2 | 1.8 | 0.1 |
| Replicate 3 | 1.6 | 0.05 | 3.5 | 2.0 | 0.1 |
| Replicate 4 | 1.5 | 0.05 | 3.0 | 2.5 | 0.1 |
| Average | 1.6 | 0.05 | 3.2 | 2.4 | 0.2 |

SD, standard deviation.
RSD, relative standard deviation.

Experiment 5

Figure 19:
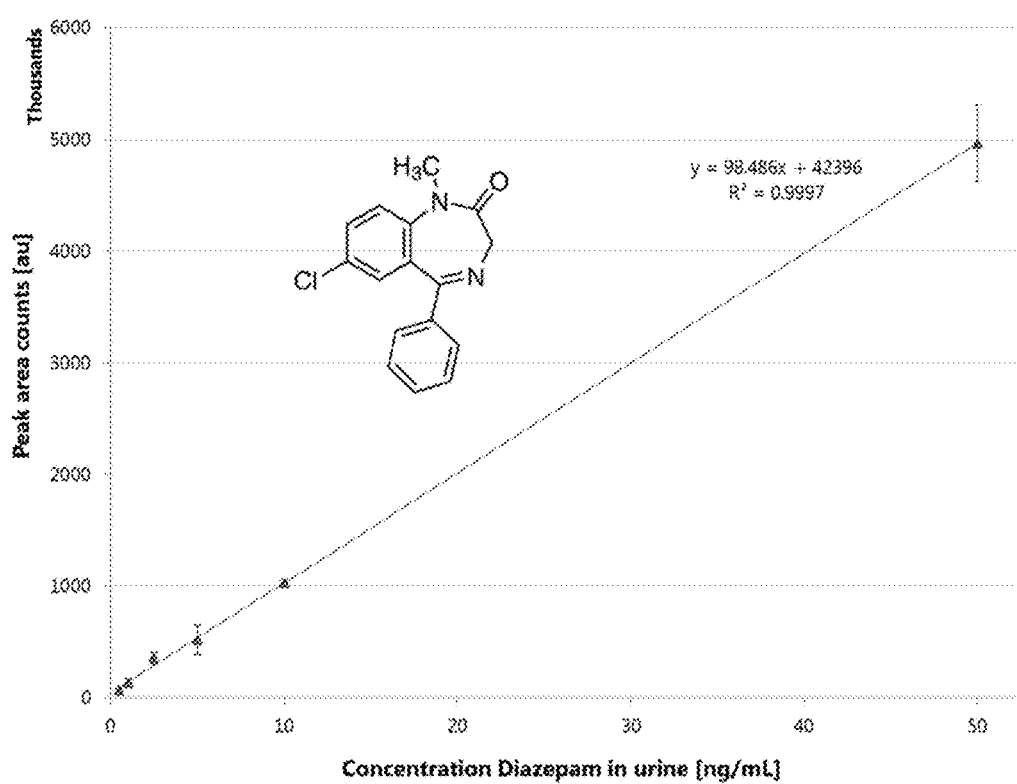
FIG. 19 is a graph that shows SPME-TM standard free calibration. Quantitative analysis of urine spiked with diazepam (500 pg mL$^{-1}$ to 50 ng mL$^{-1}$).
Figure 20:
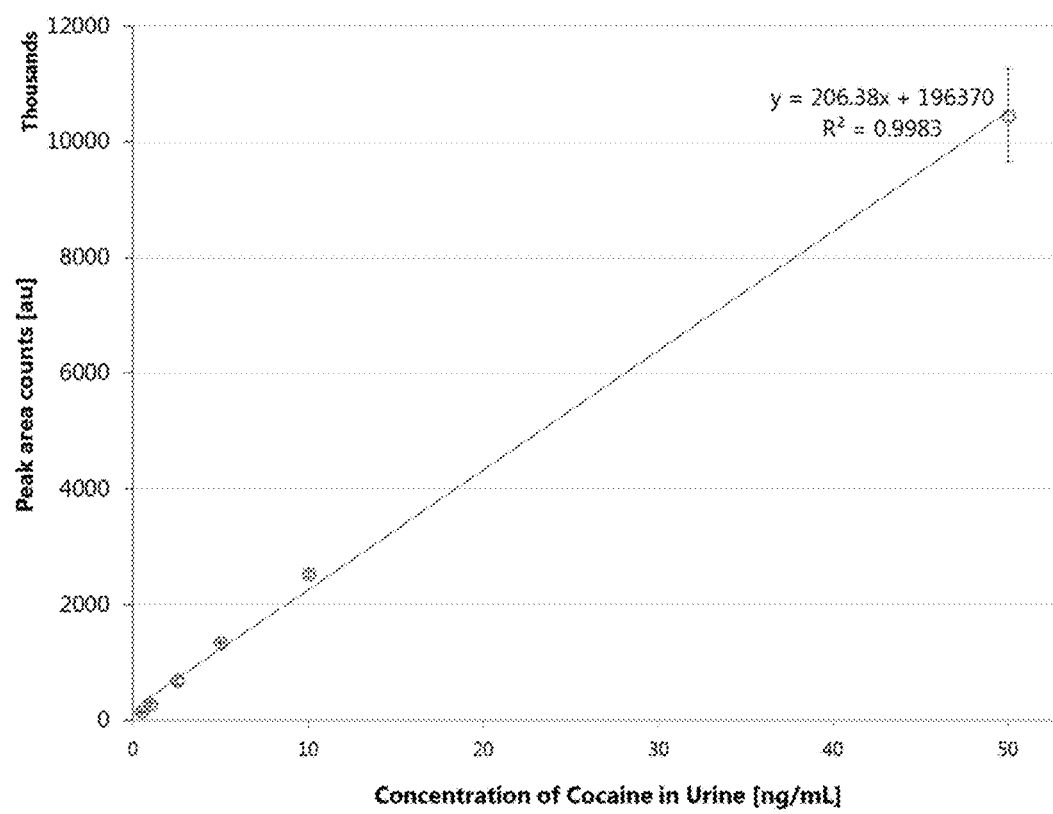
FIG. 20 is a graph that shows SPME-TM standard free calibration. Quantitative analysis of urine spiked with cocaine (500 pg mL$^{-1}$ to 50 ng mL$^{-1}$).
Figure 21:
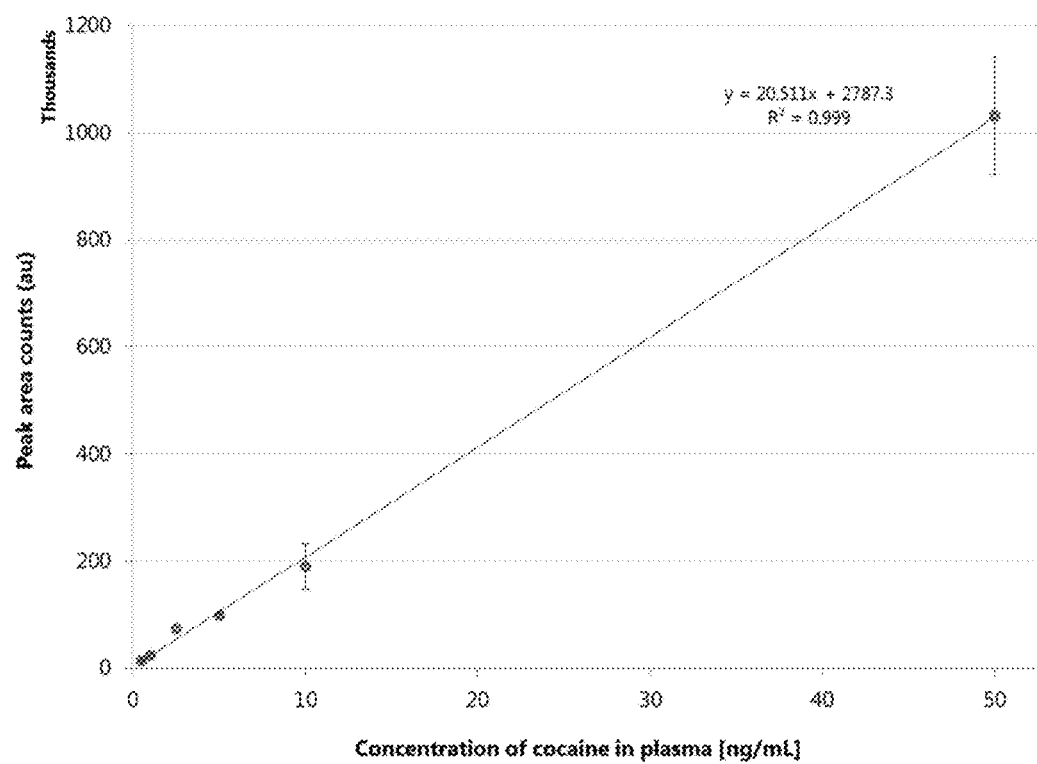
FIG. 21 is a graph that shows SPME-TM standard free calibration. Quantitative analysis of plasma spiked with cocaine (500 pg mL$^{-1}$ to 50 ng mL$^{-1}$).

Application of Exemplary Devices to the Quantitation of Drugs in Complex Matrices MS analysis provides significant amounts of information about complex samples. However, sample pre-treatment required before traditional MS analysis not only is labor-intensive and time-consuming but also intricate. Due to the speed and the easiness of the analysis when using devices and methods disclosed herein, screening of controlled substances in biological samples as well as for therapeutic drug monitoring (TDM) may be performed with less labour and/or taking less time. Devices as disclosed in Experiment 1 were used for the quantification of cocaine and DZP in urine and plasma. FIGS. 15 to 18 summarize the linearity achieved in both matrices. Similar to PBS, LOQs of 2 and 5 pg mL$^{-1}$ were determined for cocaine in urine and plasma, respectively. Thus, matrix effects are significantly reduced by the sample clean-up provided by the disclosed methods, and analytes with low binding present comparable detection limits independently of the matrix. Because salts and biomolecules that remain mechanically attached to the coated strands during the extraction are removed through the rinsing step, the rinsing step aids to extend the operative time of the mass spectrometer by providing reliably high instrumental sensitivity as well as minimizing instrument maintenance. Unlike cocaine, the LOQ for DZP in plasma (497 pg mL$^{-1}$) was significantly higher in comparison to urine and PBS (19 and 28 pg mL$^{-1}$, respectively). However, it is worth mentioning that DZP is 98% bound to plasma proteins and devices described herein only extract the free-portion of analyte present in the matrix. Last but not least important, since the TM configuration may result in a homogeneous interaction between extracted and ionizing species, standard-free quantitation is also feasible with SPME-TM (FIGS. 19-21). Nevertheless, given that extraction is not performed at equilibrium (t≤1 min), precise variables should be properly controlled in order to obtain reproducible results. Such variables include: sampling time, convection (agitation speed and homogeneity of agitation), as well as coating thickness homogeneity. The first two parameters may be controlled by using automated extraction or rinsing systems. When the coating process parameters are controlled by automation, greater reproducibility between meshes can be attained.

Experiment 6
Analysis of Multiple Controlled Substances

Figure 22A:
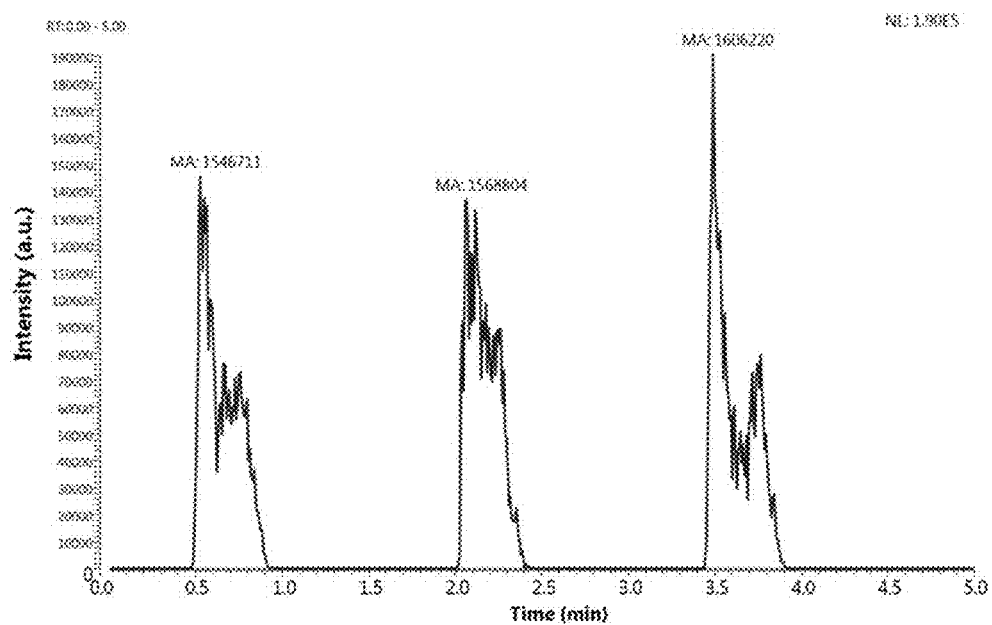
FIGS. 22A-22C show three graphs that illustrate ion chronograms of three controlled substances: heroin (FIG. 22A), propranolol (FIG. 22B), and stanozolol (FIG. 22C). 1 min extractions were performed using vortex agitator set-up at maximum speed (3200 rpm). Simultaneous extraction from 1.5 mL of PBS spiked with 20 ng mL$^{-1}$ of 21 substances described in Table 2. Analyses were performed using Thermo TSQ on MRM mode.
Figure 22B:
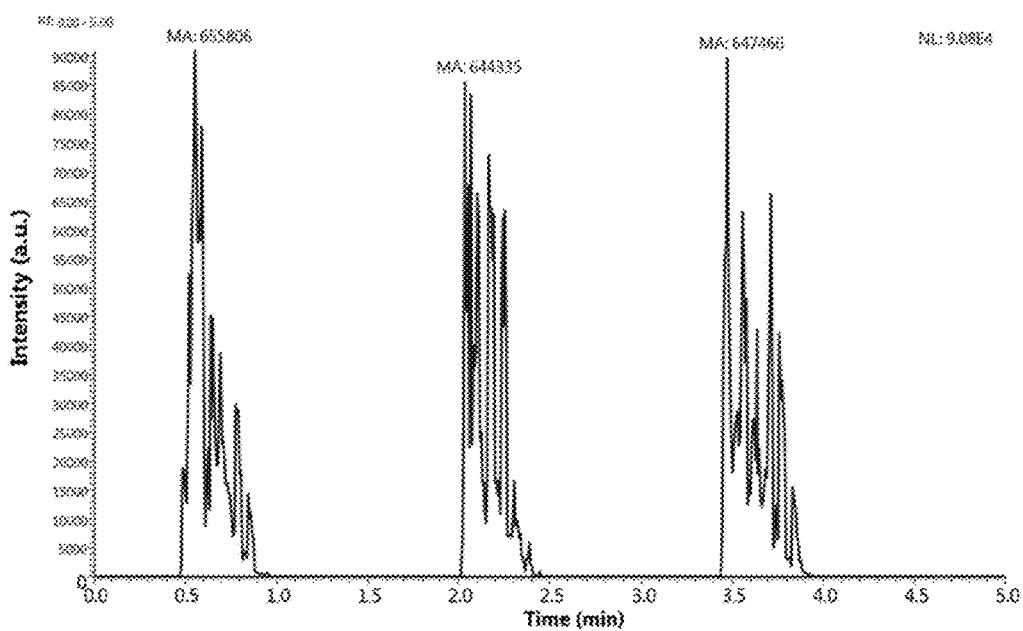
Figure 22C:
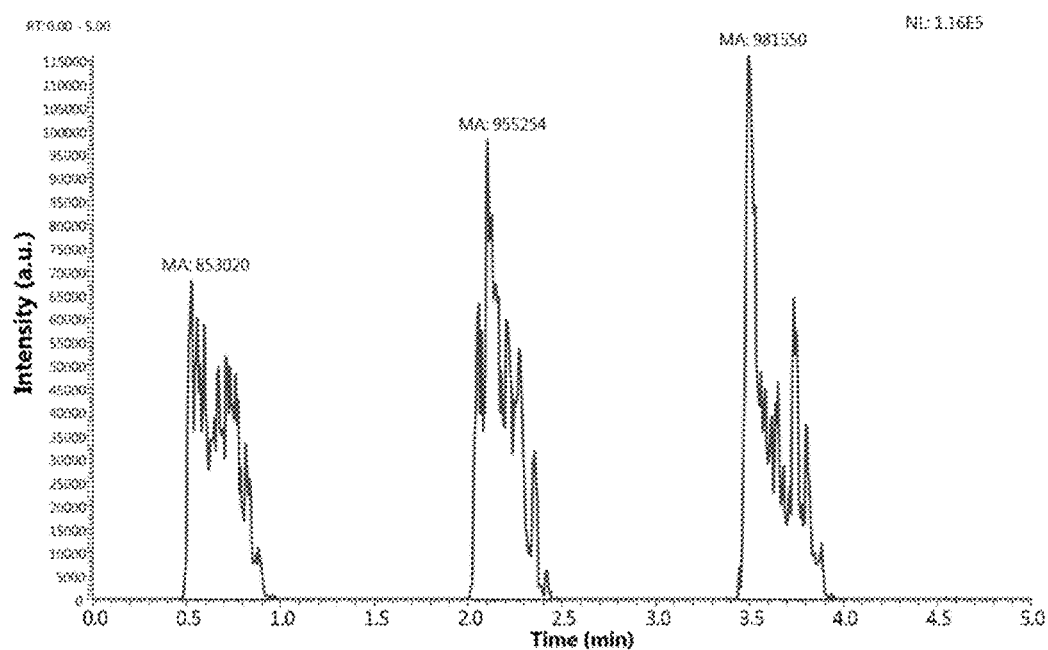

Nowadays multiple efforts are directed towards the development of powerful LC-MS/MS or GC-MS/MS methods that allow the analysis of controlled substances in complex matrices. Given the complexity of the components in the samples, such procedures entail cumbersome and extensive sample preparation steps. Consequently, approaches that allow fast, quantitative, and direct analysis are highly demanded. As a proof-of-concept, devices as described in Experiment 1 were used to simultaneously monitor 21 prohibited substances spiked in PBS at 20 ng mL$^{-1}$. Selected reaction monitoring (SRM) was used to exclusively identify each compound. LOD were tentatively predicted based on the results obtained for cocaine and diazepam in PBS (Table 6). Even though DART source parameters were not optimized for each analyte, all substances were detected and 16 compounds provided hypothetical detection limits lower than 50 pg mL$^{-1}$ (e.g. heroin [Log P 1.52], propranolol [Log P 3.48], and stanozolol [Log P 5.53]; FIGS. 22A-C). Insofar as methods and devices described in these Experiments derive their sensitivity and selectivity from the physicochemical properties of the exemplary extraction phase, other coatings with greater affinity towards specific target compounds can be used. Certainly, the ability to screen numerous substances in a single analysis using methods and devices described herein, without forfeiting sensitivity or quickness, is a noteworthy characteristic of this technique that could be used in other applications such as monitoring of personal care products in wastewaters or pesticides in food commodities.

TABLE 6

MS/MS parameters used for the analysis of 21 WADA controlled substances in positive mode, as well as instrumental response of $C_{18}$-PAN SPME-TM tandem mass spectrometry analysis. Integrated peak area obtained for a 20 ng mL$^{-1}$ solution in PBS. Average peak area (n = 3). Polarity = +.

| # | Compound name | Log P | Parent ion (m/z) | Product ion (m/z) | S-lenses | Collision energy | Average peak area | LOD* |
|---|---|---|---|---|---|---|---|---|
| 1 | Amphetamine | 1.76 | 136.099 | 91.114 | 17 | 36 | 178070 | 112 |
| 2 | Methamphetamine | 2.07 | 150.112 | 91.120 | 19 | 45 | 984694 | 20 |
| 3 | Nikethamide | 0.33 | 179.100 | 108.102 | 18 | 76 | 1160349 | 17 |
| 4 | Salbutamol | 0.64 | 240.143 | 148.103 | 18 | 59 | 13566 | 1474 |
| 5 | Propranolol | 3.48 | 260.123 | 116.138 | 17 | 89 | 649034 | 31 |
| 6 | Metoprolol | 1.60 | 268.140 | 116.146 | 18 | 94 | 184973 | 108 |
| 7 | Trenbolone | 2.27 | 271.133 | 165.106 | 56 | 97 | 647916 | 31 |
| 8 | Clenbuterol | 2.61 | 277.068 | 203.049 | 15 | 70 | 1487480 | 13 |
| 9 | Testosterone | 3.32 | 289.157 | 97.123 | 21 | 91 | 1957478 | 10 |
| 10 | Exemestane | 3.70 | 297.173 | 121.118 | 19 | 72 | 1147042 | 17 |
| 11 | Codeine | 1.20 | 300.105 | 152.092 | 64 | 104 | 438727 | 46 |
| 12 | Cocaine | 2.30 | 304.142 | 182.173 | 18 | 87 | 10975211 | 2 |
| 13 | Bisoprolol | 2.14 | 326.160 | 116.135 | 17 | 102 | 441435 | 45 |
| 14 | 6-acetylmorphine | 0.42 | 328.126 | 165.092 | 37 | 122 | 931494 | 21 |
| 15 | Stanozolol | 5.53 | 329.229 | 81.108 | 44 | 130 | 926273 | 22 |
| 16 | Strychnine | 1.93 | 335.155 | 184.129 | 36 | 136 | 604931 | 33 |
| 17 | 6-acetylcodeine | 2.08 | 342.124 | 165.092 | 45 | 165 | 2703792 | 7 |
| 18 | Formoterol | 2.20 | 345.133 | 121.090 | 32 | 85 | 24071 | 831 |
| 19 | Heroin | 1.52 | 370.133 | 165.097 | 48 | 119 | 1574345 | 13 |
| 20 | Toremifene | 6.80 | 406.210 | 72.167 | 24 | 108 | 479105 | 42 |
| 21 | GW501516 | 6.29 | 454.091 | 257.068 | 29 | 108 | 56878 | 352 |

LOD*, limit of detection estimated.

In the preceding description, for purposes of explanation, numerous details are set forth in order to provide a thorough understanding of the embodiments. However, it will be apparent to one skilled in the art that these specific details are not required. Accordingly, what has been described is merely illustrative of the application of the described embodiments and numerous modifications and variations are possible in light of the above teachings.

Since the above description provides example embodiments, it will be appreciated that modifications and variations can be effected to the particular embodiments by those of skill in the art. Accordingly, the scope of the claims should not be limited by the particular embodiments set forth herein, but should be construed in a manner consistent with the specification as a whole.

What is claimed is:

1. A device for generating ionized molecules for analysis in a mass spectrometer, the device comprising:
   a mesh substrate coated with an extraction phase of substantially uniform thickness that is from about 0.2 µm to about 50 µm, the extraction phase comprising:
      a polymer that absorbs a molecule of interest from a matrix, or
      a polymer and solid phase microextraction (SPME) particles having pores dimensioned to adsorb a molecule of interest from a matrix,
   wherein the coated mesh substrate has a sufficiently open structure to allow fluid to flow through the coated mesh substrate; and
   a solid substrate connected to the mesh substrate to provide stability to the coated mesh substrate.

2. The device according to claim 1, wherein the mesh substrate comprises a plurality of connected or impregnated wires, filaments or strings.

3. The device according to claim 2, wherein the plurality of connected or impregnated wires, filaments or strings have a diameter from 50 micrometers to 0.5 millimeters.

4. The device according to claim 2, wherein the plurality of connected or impregnated wires, filaments or strings comprise a metal, a metal alloy, or a polymer substrate.

5. The device according to claim 4, wherein the metal, metal alloy, or polymer substrate is: stainless steel, nitinol, nickel, titanium, aluminum, brass, iron, bronze, or polybutylene terephthalate.

6. The device according to claim 1, wherein the mesh substrate has an open area of at least 20%.

7. The device according to claim 1, wherein the extraction phase has a thickness sufficient to include one or two layers of particles.

8. The device according to claim 1, wherein the extraction phase is loaded with an internal standard.

9. The device according to claim 1, wherein the solid substrate comprises a metal, a metal alloy, or a polymer.

10. The device according to claim 9, wherein the solid substrate comprises stainless steel, titanium, a nickel-titanium alloy, nitinol, polybutylene terephthalate, or a 3-D printed polymer.

11. The device according to claim 1, wherein the solid substrate comprises a metal or a metal alloy and the coated mesh substrate is welded to the solid substrate.

12. The device according to claim 2, wherein the plurality of connected or impregnated wires, filaments or strings are in a grid configuration.

13. The device according to claim 6, wherein the mesh substrate has an open area of from about 50% to about 60%.

14. A mass spectrometry system comprising:
   a source of a heated gas, or a heated and metastable gas;
   an inlet for a mass spectrometer;
   a nozzle fluidly connected to the source of the heated gas, or heated and metastable gas for directing a flow of the heated gas, or heated and metastable gas to the inlet; and
   a device according to claim 1 positioned coaxial to, and at about a 0° angle from, the nozzle and the mass spectrometer inlet;
   wherein the nozzle is positioned to direct the heated gas, or heated and metastable gas through the coated mesh substrate of the device to desorb and ionize at least a portion of compounds sorbed on the coated mesh substrate, and wherein the inlet is positioned to collect and transport at least a portion of the desorbed and ionized compound to the mass spectrometer for analysis.

15. A method for analyzing an analyte previously extracted from a matrix onto a device according to claim 1, the method comprising:
   flowing a heated gas, a metastable gas, or a heated and metastable gas through the coated mesh substrate to desorb and ionize the analyte sorbed on the coated mesh substrate;
   transporting the desorbed and ionized analyte to a mass spectrometer; and
   analyzing the ionized analyte by mass spectrometry.

16. The method according to claim 15, further comprising rinsing the coated mesh substrate with a rinsing solution at least once before flowing the heated gas, metastable gas, or heated and metastable gas through the coated mesh substrate.

17. The method according to claim 15, wherein the desorbing is performed along the coated mesh substrate to characterize a distribution gradient of analytes along the coated mesh substrate.

18. A method for measuring or identifying one or more component of interest in a sample, said method comprising the steps of:
   positioning a device according to claim 1 in the sample;
   adsorbing the one or more component of interest onto the extraction phase;
   removing the device from the sample; and
   exposing the device to sufficient energy to desorb and ionize the one or more component of interest, resulting in ionization and desorption of the one or more component of interest from the extraction phase into a mass spectrometer for measurement or identification.

19. The method according to claim 18, wherein exposing the device to sufficient energy to desorb and ionize the one or more component of interest comprises exposing the mesh substrate to a laser or a hot carrier gas.

20. A holder positioning one or more devices according to claim 1 between a nozzle that is fluidly connected to a source of a heated gas, a metastable gas, or a heated and metastable gas, and an inlet for a mass spectrometer so that ionized molecules desorbed from the coated mesh substrate are transported to the mass spectrometer, the holder comprising:
   connectors for each of the one or more devices, each of the connectors releasably securing one of the devices.

21. The holder according to claim 20, wherein the holder is sized and shaped to simultaneously hold up to twelve devices according to claim 1, and is sized and shaped to be fitted on an automated electrical actuator that positions the coated mesh substrate between the nozzle and the inlet for the mass spectrometer.

* * * * *